United States Patent
O'Neill et al.

(10) Patent No.: US 12,310,979 B2
(45) Date of Patent: *May 27, 2025

(54) INHALABLE FORMULATION OF FLUTICASONE PROPIONATE AND ALBUTEROL SULFATE

(71) Applicant: NORTON (WATERFORD) LIMITED, Waterford (IE)

(72) Inventors: Brian Paul O'Neill, Waterford (IE); Hardik Kirtikumar Shah, Waterford (IE); Julian Alexander Blair, Waterford (IE); Chris David Edlin, Waterford (IE); Shane Michael McKeon, Waterford (IE)

(73) Assignee: NORTON (WATERFORD) LIMITED, Waterford (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/139,031

(22) Filed: Apr. 25, 2023

(65) Prior Publication Data
US 2023/0255983 A1  Aug. 17, 2023

Related U.S. Application Data

(63) Continuation of application No. 17/410,774, filed on Aug. 24, 2021, now Pat. No. 11,638,710, which is a continuation of application No. PCT/EP2021/072718, filed on Aug. 16, 2021.

(30) Foreign Application Priority Data

Aug. 14, 2020 (GB) ..................................... 2012742

(51) Int. Cl.
| | |
|---|---|
| A61K 31/569 | (2006.01) |
| A61K 9/00 | (2006.01) |
| A61K 9/16 | (2006.01) |
| A61K 31/137 | (2006.01) |
| A61K 47/26 | (2006.01) |
| A61M 15/00 | (2006.01) |
| A61P 11/08 | (2006.01) |

(52) U.S. Cl.
CPC .......... *A61K 31/569* (2013.01); *A61K 9/0075* (2013.01); *A61K 9/1623* (2013.01); *A61K 9/1694* (2013.01); *A61K 31/137* (2013.01); *A61K 47/26* (2013.01); *A61M 15/0008* (2014.02); *A61M 15/0065* (2013.01); *A61M 2202/064* (2013.01); *A61M 2206/16* (2013.01)

(58) Field of Classification Search
CPC .. A61K 31/569; A61K 9/0075; A61K 31/137; A61K 47/26; A61M 15/0065; A61P 11/08
See application file for complete search history.

(56) References Cited

U.S. PATENT DOCUMENTS

| | | | |
|---|---|---|---|
| 8,778,402 B2 | 7/2014 | Monari et al. | |
| 9,439,862 B2 | 9/2016 | Weers et al. | |
| 11,638,710 B2* | 5/2023 | O'Neill | A61M 15/0008 |
| | | | 424/489 |
| 2009/0291146 A1 | 11/2009 | Roche et al. | |
| 2011/0139152 A1 | 6/2011 | Morton et al. | |
| 2012/0071449 A1 | 3/2012 | Kanlag et al. | |
| 2014/0065219 A1 | 3/2014 | Bosch et al. | |
| 2015/0099726 A1 | 4/2015 | Dalvi et al. | |
| 2016/0271345 A1 | 9/2016 | Blair et al. | |
| 2017/0239177 A1 | 8/2017 | Dalvi et al. | |
| 2021/0293715 A1 | 9/2021 | Shah | |
| 2022/0047610 A1 | 2/2022 | O'Neill et al. | |
| 2024/0033222 A1* | 2/2024 | O'Neill | A61P 11/08 |

FOREIGN PATENT DOCUMENTS

| | | |
|---|---|---|
| AU | 2015331915 | 5/2017 |
| CN | 102149438 | 8/2011 |
| CN | 102946868 | 10/2014 |
| EP | 2738172 | 6/2014 |
| KR | 20170118975 | 10/2017 |
| WO | 2011120779 | 10/2011 |
| WO | 2013/075086 | 5/2013 |
| WO | 2015086278 | 6/2015 |
| WO | 2016061448 | 4/2016 |
| WO | 2020031119 | 2/2020 |

OTHER PUBLICATIONS

Kerwin et al (Pharmacokinetics, pharmacodynamics, efficacy, and safety of albuterol (salbutamol) multi-dose dry-powder Inhaler and ProAir® Hydrofluoroalkane for the treatment of persistent asthma: results of two randomized double-blind studies). Clin Drug Investig (2016) 63:55-65. (Year: 2016).*

Pocket guide for asthma management and prevention (GINA) . (Year: 2018).*

Global initiative for chronic obstructive lung disease (Gold). (Year: 2017).*

Extended European Search Report issued in corresponding European Patent Application No. 2118187 4.5, dated Jul. 27, 2021.

Allan, P. et al.; "In situ monitoring of powder blending by non-invasive Raman spectrometry with wide area illumination", vol. 76, Mar. 2013, pp. 28-35.

Debeer, T. et al.; "Near infrared and Raman spectroscopy for the in-process monitoring of pharmaceutical production processes", International Journal of Pharmaceutics, vol. 417, Sep. 2011, pp. 32-47.

(Continued)

*Primary Examiner* — Mina Haghighatian
(74) *Attorney, Agent, or Firm* — Pillsbury Winthrop Shaw Pittman, LLP

(57) ABSTRACT

This invention relates to a fixed-dose dry powder inhalation formulation comprising fluticasone propionate and albuterol sulfate, together with an α-lactose monohydrate carrier. In the formulation, the albuterol sulfate stabilises fluticasone propionate.

3 Claims, 16 Drawing Sheets

(56) References Cited

OTHER PUBLICATIONS

Wang, H. et al.; "Macro-Raman spectroscopy for bulk composition and homogeneity analysis of multi-component pharmaceutical powders", Journal of Pharmaceutical and Biomedical Analysis, vol. 141, Apr. 23, 2017, pp. 180-191.
Riolo, D. et al.; "Raman spectroscopy as a PAT for pharmaceutical blending: Advantages and disadvantages", Journal of Pharmaceutical and Biomedical Analysis, vol. 149, Feb. 2018, pp. 329-334.
International Search Report and Written Opinion issued in corresponding PCT Patent Application No. PCT/IB2019/056737, dated Nov. 27, 2019.
International Preliminary Report on Patentability and Written Opinion issued in corresponding International Application No. PCT/IB2019/056737 on Feb. 9, 2021.
Albuterol as a Beta2 Agonists, downloaded from: https://www.aaaai.org/Tools-for-the-Public/Allergy,-Asthma-Immunology-Glossary/Beta2-agonists-Defined.
Written Opinion of the International Searching Authority for PCT/EP2021/072718 dated Aug. 16, 2021, 9 pages.
Guchardi et al., "Influence of fine lactose and magnesium stearate on low dose dry powder inhaler formulations", Novartis Pharma AG, Inhalation Development and Technology, CH-4002 Basel, Switzerland, received in revised form Jun. 25, 2007; accepted Jun. 27, 2007, Available online Jul. 1, 2007.
El-Gendy et al., "Nanoparticle agglomerates of fluticasone propionate in combination with albuterol sulfate as dry powder aerosols", Elsevier; European Journal of Pharmaceutical Sciences 44 (2011) 522-533. (Year: 2011).
Highlights of Prescribing Information, "Advair HFA", Food and Drug Administration, pp. 1-54 (Jul. 2023).
I. Axelsson et al., "Effets of inhaled corticosteroids on growth in children with persistent asthma: Impact of drug molecules and delivery devices—An overview of Cochrane reviews", ScienceDirect, Paediatric Respiratory Review, 32, pp. 28-29 (2019).
Highlights of Prescribing Information, "Flovent Diskus", Food and Drug Administration, pp. 1-33 (Aug. 2023).
D. B. Allen, "Inhaled Corticosteroids and Endocrine Effects in Childhood", Endocrinol. Metab. Clin. N. Am., 49. pp. 651-665 (2020).
I. Axelsson et al., Inhaled corticosteroids in children with persistent asthma: effects of different drugs and delivery devices on growth, Cochrane Database of Systematic Reviews, Issue 6, pp. 1-38 (2019).
"The Changing Role of Inhaled Corticosteroids in Asthma Management", NIH Publication, No. 20-HL-8148, pp. 1-3 (Dec. 2020).
M. Blaiss et al., "Safety of ciclesonide in children with asthma: A review of randomized controlled trials", Allergy and Asthma Proceedings, vol. 42, No. 6, pp. 471-480 (Nov. 2021).
U. Nalin et al., "Single inhaler maintenance and reliever therapy in pediatric asthma", Current Opinion, Review, vol. 19, No. 2 pp. 1-7 (Apr. 2019).
Highlights of Prescribing Information, Symbicort®, AstraZeneca, pp. 1-18 (Dec. 2017).
The Pharmacological Basis of Therapeutics, "Glucocorticoids", Pharma Therapy of Asthma, Chapter 27, pp. 721-722 (2006).
Patent Examination Report issued in corresponding New Zealand Application No. 797404, dated Mar. 10, 2025.

\* cited by examiner

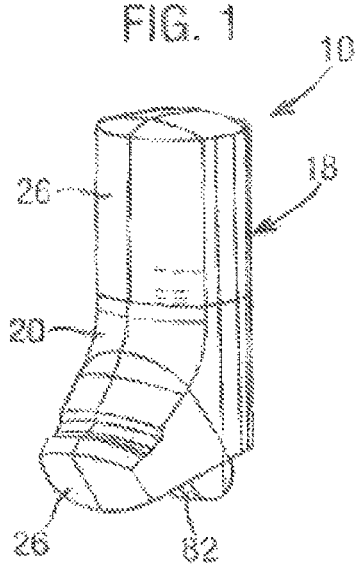
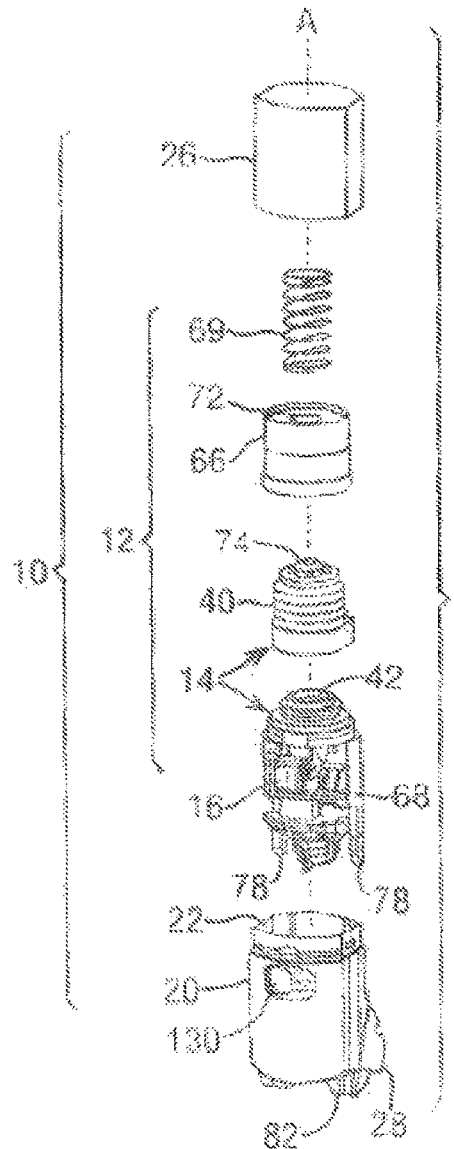

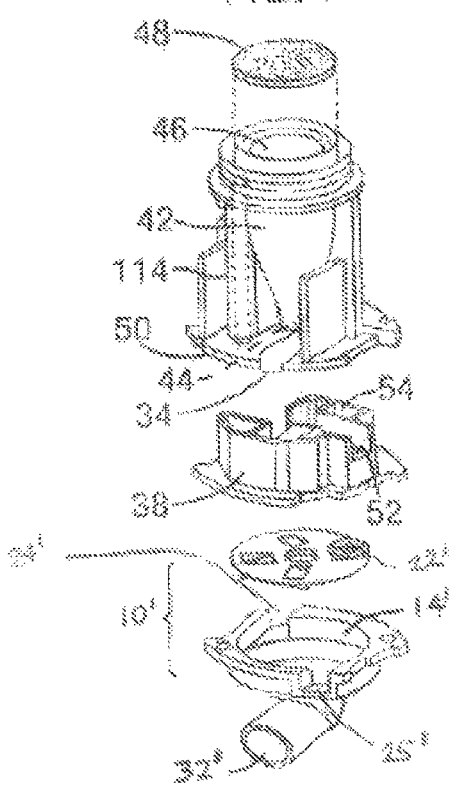
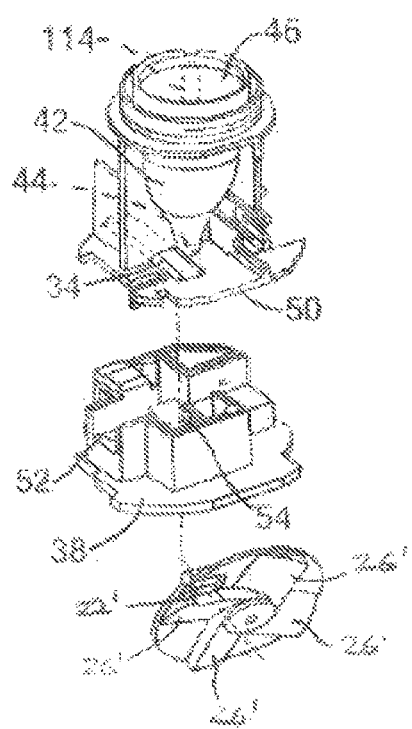

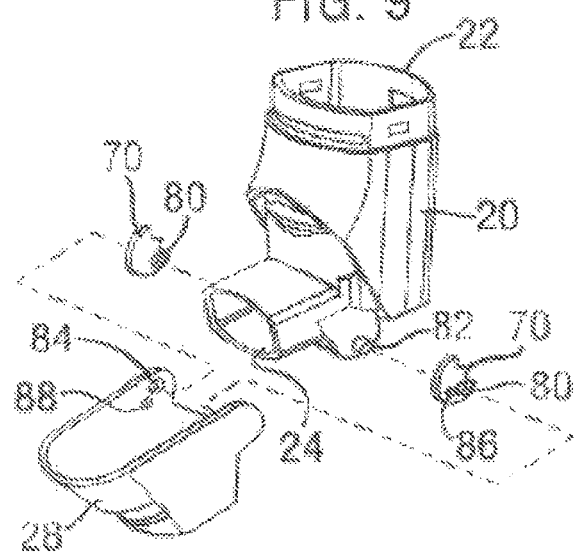
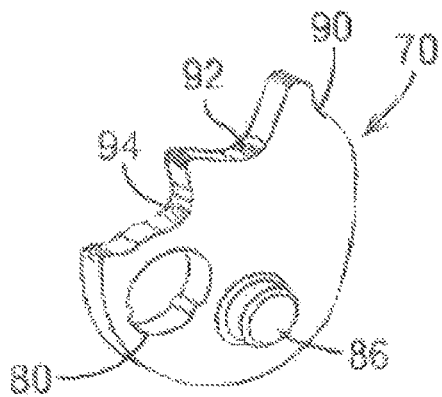

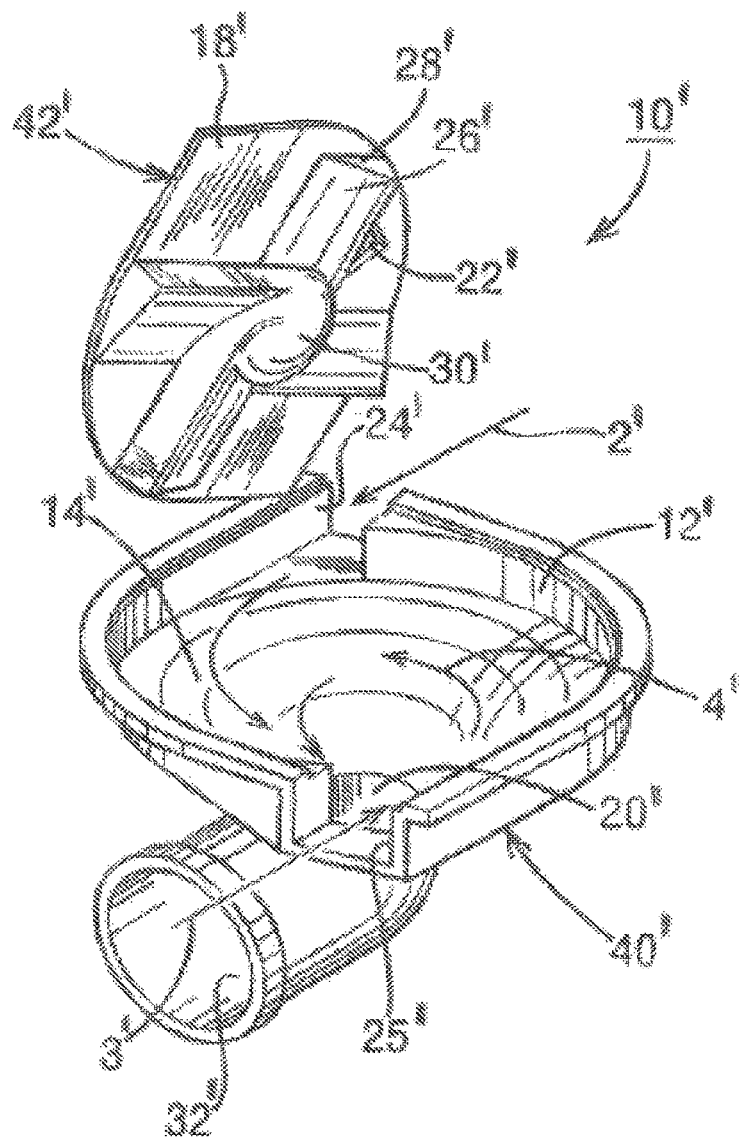

INHALABLE FORMULATION OF FLUTICASONE PROPIONATE AND ALBUTEROL SULFATE

CROSS REFERENCE TO RELATED APPLICATION

This application is a continuation of U.S. application Ser. No. 17/410,774, filed on Aug. 24, 2021, entitled "An Inhalable Formulation of Fluticasone Propionate and Albuterol Sulfate," which is a continuation of International Patent Application No. PCT/EP2021/072718 filed Aug. 16, 2021, entitled "An Inhalable Formulation of Fluticasone Propionate and Albuterol Sulfate," which claims the benefit of GB Patent Application No. 2012742.9 filed Aug. 14, 2020 entitled "An Inhalable Formulation of Fluticasone Propionate and Albuterol Sulfate," the disclosures of all of which are incorporated by reference herein in its entirety.

This invention relates to an inhalable formulation, and particularly to a fixed-dose composition containing fluticasone and albuterol.

Inhaled corticosteroids and short-acting $\beta_2$-agonists represent two classes of active ingredient that have been developed to treat respiratory disorders (e.g. asthma ad COPD). Each class has differing targets and effects.

Inhaled corticosteroids (ICSs) are steroid hormones used in the long-term control of respiratory disorders. They function by reducing the airway inflammation. They are often termed "controller" or "maintenance" medicines.

One example is fluticasone. Fluticasone is an inhaled corticosteroid indicated for the treatment of asthma and allergic rhinitis. It is also used to treat eosinophilic esophagitis. It is named as S-(fluoromethyl)-6α,9-difluoro-11β, 17-dihydroxy-16α-methyl-3-oxoandrosta-1,4-diene-17β-carbothioate-17-propanoate. Fluticasone is typically administered as the propionate salt, the structure of which is well-known in the art.

Short-acting $\beta_2$-agonists (SABAs) are examples of bronchodilators, and are employed to dilate the bronchi and bronchioles, decreasing resistance in the airways, and thereby increasing the airflow to the lungs. Bronchodilators may be short-acting or long-acting. Short-acting bronchodilators provide a rapid relief from acute bronchoconstriction (and are often called "rescue" or "reliever" medicines), whereas long-acting bronchodilators help control and prevent longer-term symptoms.

Albuterol (also known as salbutamol) is a short-acting $\beta_2$-agonist that is indicated for the treatment of asthma. It is named as 4-[2-(tert-butylamino)-1-hydroxyethyl]-2-(hydroxymethyl)-phenol. Albuterol is typically administered as the sulfate salt, the structure of which is well-known in the art.

These two classes of active ingredient have specifically been developed in response to the need for the treatment and management of respiratory disorders, and particularly asthma and chronic obstructive pulmonary disease (COPD).

According to the Global Initiative for Asthma (GINA) guidelines, a step-wise approach is taken to treatment. At step 1, which represents a mild form of asthma, the patient is given an as needed SABA, such as albuterol sulfate. At step 2, a regular low-dose ICS is given alongside the SABA. At step 3, a LABA (L is long) is added. At step 4, the doses are increased and at step 5, further add on treatments are included.

An analogous stepwise treatment is set out in the Global Initiative for Chronic Obstructive Lung Disease (GOLD) guidelines.

A number of approaches have been taken in preparing and formulating these active ingredients for delivery by inhalation, such as via a dry powder inhaler (DPI), a pressurised metered dose inhaler (pMDI) or a nebuliser.

In order to facilitate delivery into the lung, the micronised active ingredient is adhered to the surface of the coarse carrier and, on inhalation, the active ingredient separates from the coarse carrier and is entrained into the lung (this is discussed in more detail herein below with reference to FIG. 23). The coarse carrier particles are of a size that, after inhalation, most of them remain in the inhaler or deposit in the mouth and upper airways. In order to reach the lower airways, active ingredient particles must therefore detach from the carrier particles and become re-dispersed in the air flow.

High-energy, micronised active ingredient particles are highly cohesive and form larger unstable agglomerates. The formation of such agglomerates contributes to poor powder flow and homogeneity, accelerated chemical degradation and causes suboptimal adhesion/dispersion (to/from the carrier). These factors are the cause of unwanted variations in the release profile of the active ingredients when formulated as inhalable dry powder therapies, and ideally need to be avoided.

Dry powder inhalable formulations containing fluticasone propionate or albuterol sulfate are known.

Fluticasone propionate (Fp) is for example marketed as Flixotide® Accuhaler® and Flixotide® Diskhaler®. Flixotide Accuhaler contains a mixture of microfine fluticasone propionate (50, 100, 250 or 500 micrograms (µg)) and larger particle size lactose.

Albuterol sulfate is for example marketed as Ventolin® Accuhaler® and Easyhaler®, Ventolin® Accuhaler® contains a mixture of microfine albuterol sulfate (200 µg) and larger particle size lactose.

Fixed-dose combination inhalers can be provided to improve patient compliance and convenience. However, the formulator has to ensure that the formulations are compatible and that a reasonable shelf-life can be obtained.

Stability is particularly important for all formulations, and an increase in stability (both chemical and physical) provides prolonged pharmaceutical performance and concomitantly prolonged shelf life which improves patient convenience and reduces wastage.

Fluticasone propionate is difficult to formulate as a dry powder formulation. In this regard, a dry powder formulation typically contains a micronised active ingredient and a coarse carrier. The active ingredient needs to be in micronised form (typically a mass median aerodynamic diameter of 1-10 µm, more typically 2-5 µm). This size of particle is able to penetrate the lung on inhalation. However, such particles have a high surface energy and require a coarse carrier in order to be able to meter the formulation. The coarse carrier is typically lactose, usually in the form of α-lactose monohydrate.

The high surface energy of the active ingredient can affect the stability of the dry powder product over time.

Micronised fluticasone propionate is particularly sensitive to environmental conditions once the product has been removed from its protective packaging. For example, temperature and humidity have deleterious effects upon the aerodynamic particle size distribution (APSD) and fine particle fraction (FPF) of the dry powder formulation. For this reason, the fluticasone propionate mono product (ArmonAir® Respiclick, 55 mcg) is typically marketed with a so-called "out-of-pouch shelf life" of 1 month and the fluticasone propionate mono product (ArmonAin®, 25 mcg, Phase IIB) has been proven to have an "out-of-pouch shelf life" of 2 months.

In contrast, the albuterol product (ProAir Respiclick®, 90 mcg) is more stable and has a longer out-of-pouch shelf life of 13 Months. Consequently, formulating combination products containing an ICS and a SABA is challenging. For example, the in-use stability of fluticasone propionate (when formulated with a SABA) would require extension to better match that of the SABA. Without this extension, the stability of the combination product is governed solely by the least stable active ingredient (i.e. for fluticasone propionate, ArmonAir® Respiclick).

There remains a need in the art for a dry powder inhalable formulation containing fluticasone propionate and albuterol sulfate which does not suffer the drawback of a short in-use shelf-life. There also remains a need in the art to treat asthma symptoms by way of a combination product of fluticasone propionate and albuterol sulfate.

Accordingly, the present invention provides a dry powder inhalable formulation comprising fluticasone propionate, albuterol sulfate and an α-lactose monohydrate carrier.

It has been suggested that albuterol sulfate has a stabilising effect on fluticasone propionate when formulated with an α-lactose monohydrate carrier. Formulation development work was carried out to increase the in-use shelf life of fluticasone propionate in combination with albuterol sulfate. The formulation was also developed to ensure that both molecules are compatible.

The formulation displays an advantageous stability profile, is resistant to degradation and demonstrates prolonged pharmaceutical performance and in-use shelf life (in comparison to the respective mono-products).

The invention will now be described in detail with reference to the accompanying drawings, in which:

FIG. 1 is a first side isometric view of a dry powder inhaler according to a preferred embodiment;

FIG. 2 is an exploded, second side isometric view of the inhaler of FIG. 1;

FIG. 7 is an exploded first side isometric view of a hopper and a deagglomerator of the inhaler of FIG. 1;

FIG. 8 is an exploded second side isometric view of the hopper and a swirl chamber roof of the deagglomerator of the inhaler of FIG. 1;

FIG. 9 is an exploded first side isometric view of a case, cams and a mouthpiece cover of the inhaler of FIG. 1;

FIG. 10 is an enlarged side isometric view of one of the cams of the inhaler of FIG. 1;

FIG. 17 is an exploded isometric view of a deagglomerator according to the present disclosure;

Figure 23:
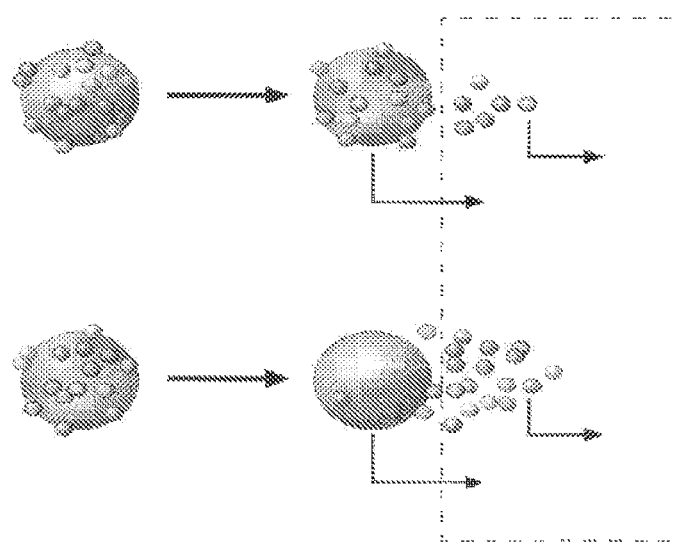
Figure 24:
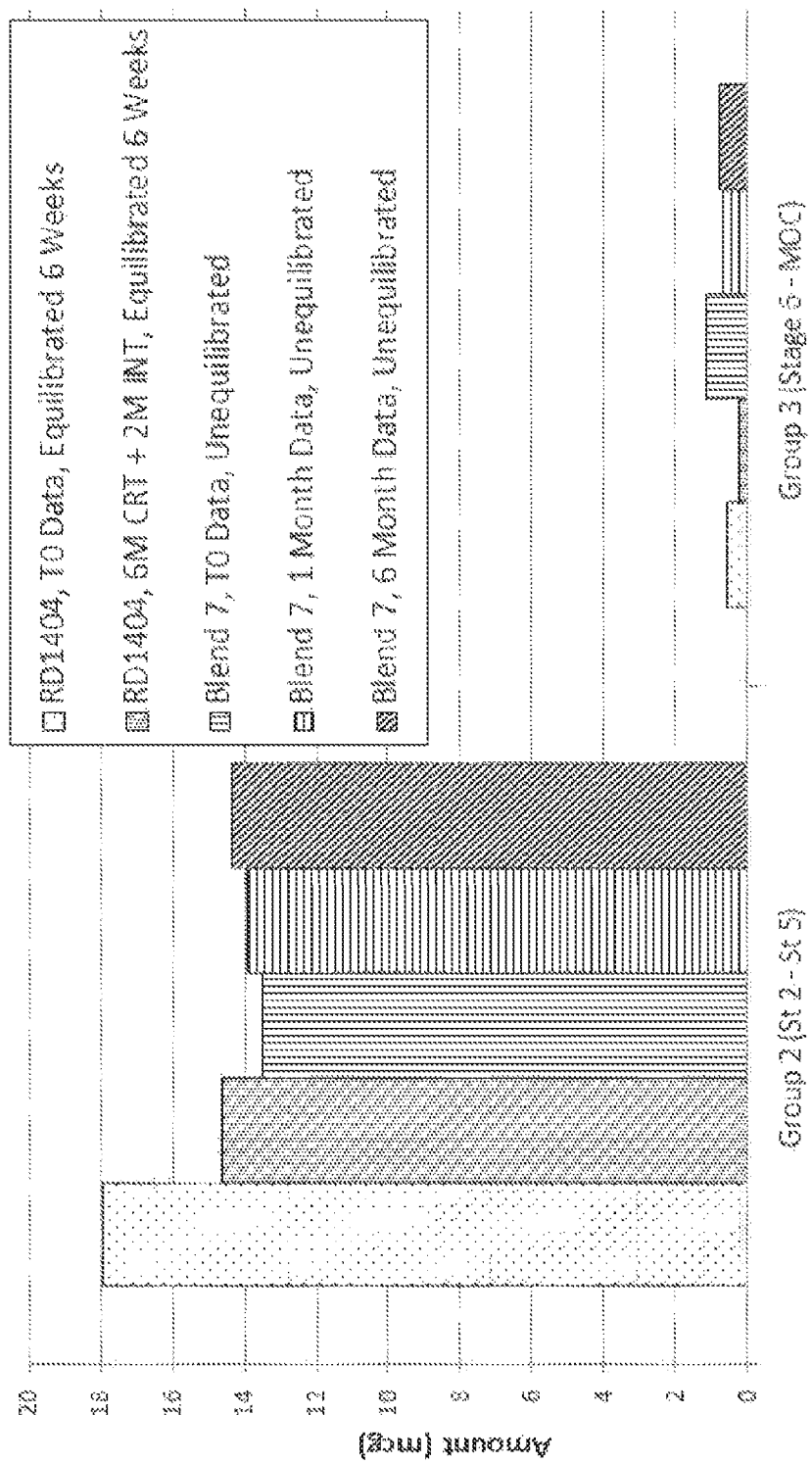
Figure 25:
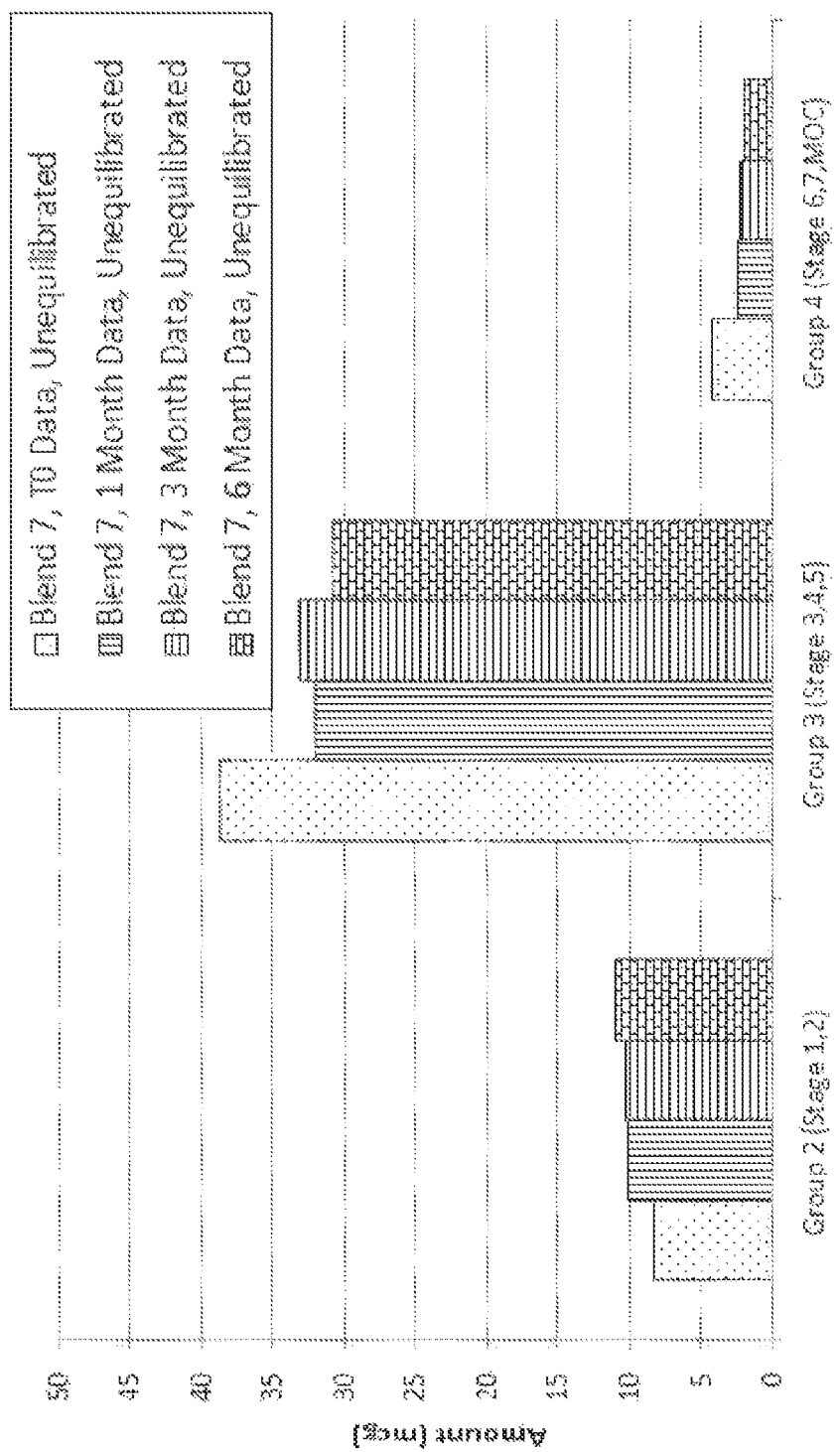
Figure 26:
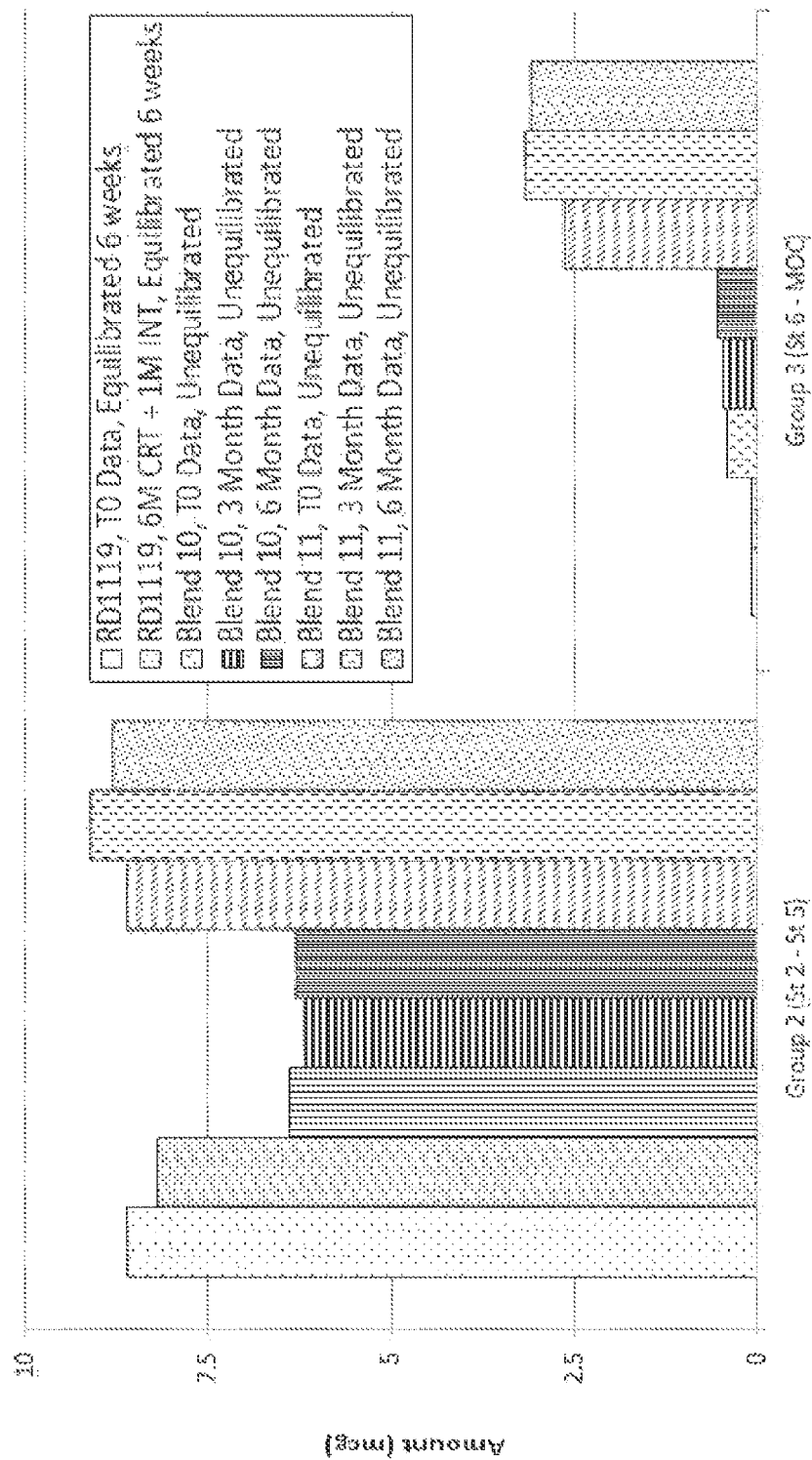
Figure 27:
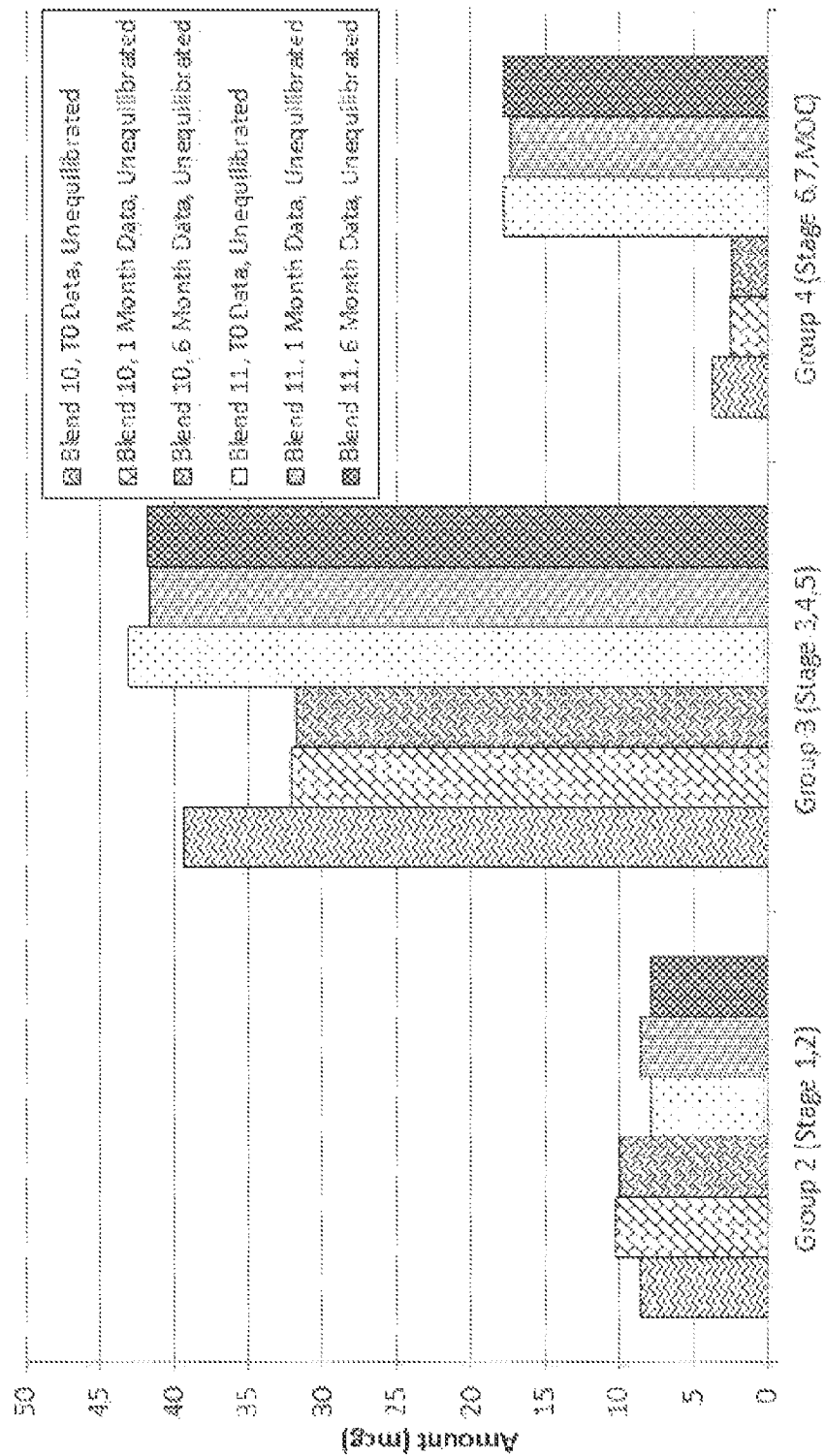

FIG. 23 shows entrainment of an inhalable dry powder formulation into an airstream and detachment of micronised active ingredient from a coarse carrier under conditions of strong and weak adhesion (see Particulate Interactions in Dry Powder Formulations for Inhalation, X. M. Zeng et al. Taylor & Francis, London, 2000);

FIG. 24 shows a graphical representation of the in-use stability (30° C./65% RH, Unwrapped) of fluticasone propionate in registration ArmonAir Respiclick Batch RD1404 (fluticasone propionate mono-product) and blend 7 (fluticasone propionate+albuterol sulfate combination product);

FIG. 25 shows a graphical representation of the in-use stability (30° C./65% RH, Unwrapped) of albuterol for blend 7 (fluticasone propionate+albuterol sulfate combination product);

FIG. 26 shows a graphical representation of the in-use stability (30° C./65% RH, Unwrapped) of fluticasone propionate in Phase IIB ArmonAir Development Batch RD1119 (fluticasone propionate mono-product), blend 10 (fluticasone propionate+albuterol sulfate combination product), and blend 11 (fluticasone propionate+albuterol sulfate combination product with magnesium stearate); and FIG. 27 shows a graphical representation of the in-use stability (30° C./65% RH, Unwrapped) of albuterol in blend 10 (fluticasone propionate+albuterol sulfate combination product) and blend 11 (fluticasone propionate+albuterol sulfate combination product with magnesium stearate).

This invention relates to a fixed-dose dry powder inhalation formulation comprising fluticasone propionate and albuterol sulfate, together with an α-lactose monohydrate carrier. In the formulation, the albuterol sulfate is thought to help stabilise fluticasone propionate.

Micronised active pharmaceutical ingredients typically have high surface energy (primarily resulting from their small particle size and hence large surface area). A secondary contributor to surface energy originates from inherent electrostatic effects, which are a product of the chemical composition and structural architecture of an active ingredient. The electrostatic properties and behaviour of a particular compound result from Van der Waals forces (distance dependent interactions between atoms) which are known to be responsible for inter alia cohesion within powders.

Consequently, the chemical composition and structural architecture of an active ingredient will determine its electrostatic makeup and thus its stability based upon the inter- and intra-particle interactions with neighbouring particles and the broader environment (e.g. atmospheric water vapour).

Micronised fluticasone propionate is known to be particularly problematic to the extent that it has a short shelf life. It is understood that micronised fluticasone propionate suffers from physical instability, and will adsorb moisture and change surface properties which leads to a reduction in FPF when stored at the in-use conditions. Therefore, it is difficult for the formulator to control the stability of micronised powders. For example, the size reduction step is necessary to break down particles into a smaller size (i.e. inhalable size) but a by-product of the step is that the amount of electrostatic energy within the bulk powder can be increased, which can increase the likelihood of degradation.

The present invention improves the physical stability of fluticasone propionate in the presence of an α-lactose monohydrate carrier by mixing fluticasone propionate with albuterol sulfate. The pharmaceutical performance and thus in-use shelf life of fluticasone propionate is extended in comparison to the mono-product.

Thus, the combination of fluticasone propionate, albuterol sulfate and α-lactose monohydrate displays enhanced physical stability (i.e. less coarsening) whilst the product is out-of-pouch in comparison to the mono-product of fluticasone propionate and α-lactose monohydrate, and allows formulation of an advantageous dry powder combination inhalable formulation.

It has been found that the present invention increases the physical stability of fluticasone propionate. The data (see, Tables 1 and 2, and FIGS. 24-27) suggest that the equilibration step of 6 weeks (30° C./65% RH, Unwrapped) that is currently used for the ArmonAir Respiclick mono-products can be reduced to 4 weeks for the ICS:SABA (fluticasone propionate:albuterol sulfate) MDPI combination products (55/90 mcg and 25/90 mcg). Based on this evaluation, it can be suggested that an in-use shelf-life of 5 months can be achieved based on the introduction of an equilibration step of 4 weeks.

It is preferred that the weight ratio of albuterol sulfate to fluticasone propionate is from 1.0-10.0 to 1.0 by total weight of the formulation. It is also preferred that the weight ratio of albuterol sulfate to fluticasone propionate is from 2.0-5.0 to 1.0. It is most preferred that the weight ratio of albuterol sulfate to fluticasone propionate is from 3.5-5.0 to 1.0 by total weight of the formulation. These ratios are particularly advantageous in terms of the stability of fluticasone propionate and therefore the dry powder inhalable formulation.

The particle sizes (mass median aerodynamic diameter, MMAD) of the fluticasone propionate and albuterol sulfate used within the process of the present invention are each less than 10 µm in size, more preferably 1-4 µm. MMAD may be measured using a next generation impactor (NGI).

This particle size ensures that the particles effectively adhere to the α-lactose monohydrate during mixing, and also that the particles disperse and become entrained in the air stream and deposited in the lower lung (i.e. upon actuation of an inhaler device).

Preferably, the particle size distribution of the inhaled fluticasone propionate is d10=0.4-1.0 µm, d50=1.0-3.0 µm, d90=2.5-7.5 µm and NLT99%<10 µm. Most preferably the particle size distribution of the inhaled fluticasone propionate is d10=0.5-0.9 µm, d50=1.5-2.5 µm, d90=4.1-6.2 µm and NLT99%<10 µm. The span value (calculated) is preferably 1.2-3.8.

The particle size of the fluticasone propionate may be measured by laser diffraction as an aqueous dispersion, e.g. using a Malvern Mastersizer 2000 instrument. In particular, the technique is wet dispersion. The equipment is set with the following optical parameters: Refractive index for fluticasone propionate=1.530, Refractive index for dispersant water=1.330, Absorption=3.0 and Obscuration=10-30%. The sample suspension is prepared by mixing approximately 50 mg sample with 10 mL of de-ionized water containing 1% Tween 80 in a 25 mL glass vessel. The suspension is stirred with a magnetic stirrer for 2 min at moderate speed. The Hydro 2000S dispersion unit tank is filled with about 150 mL de-ionized water. The de-ionized water is sonicated by setting the ultrasonics at the level of 100% for 30 seconds and then the ultrasonic is turned back down to 0%. The pump/stirrer in the dispersion unit tank is turned to 3500 rpm and then down to zero to clear any bubbles. About 0.3 mL of 1% TA-10X FG defoamer is added into the dispersion media and the pump/stirrer is turned to about 2000 rpm and then the background is measured. The prepared suspension samples are slowly dropped into the dispersion unit until a stabilized initial obscuration at 10-20% is reached. The sample is continued to be stirred in the dispersion unit for about 1 min at 2000 rpm, then the ultrasound is turned on and the level set to 100%. After sonicating for 5 min with both the pump and ultrasound on, the sample is measured three times. The procedure is repeated two more times.

Preferably, the particle size distribution of the albuterol sulfate is d10=0.4-1.0 µm, d50=1.0-3.0 µm, d90=2.5-9.0 µm and NLT99%. Most preferably the albuterol sulfate is d10=0.6-0.7 µm, d50=1.1-1.7 µm, d90=2.4-3.8 µm and NLT99%<10 µm. The span value (calculated) is preferably 1.5-2.0.

The particle size distribution of the albuterol sulfate may be measured by laser diffraction as a dry dispersion, e.g. using a Sympatec HELOS/BF equipped with a RODOS disperser and ROTARY feeder. In particular, lens type R3: 0.5/0.9 . . . 175 µm is used. The following information is set on the equipment: density=3.2170 g/cm$^3$; shape factor=1.00, calculation mode=HRLD, forced stability=0, limit curves=not used. The following trigger conditions are set: Name=Channel 28> or =2%, reference duration=10 s (single), time base=100 ms, focus prior to measurement=No, normal measurement=standard mode, start=0.000 s, Channel 28> or =2%, valid=always, stop after=5 s, channel 28< or =2%, or after=99.000 s, real time, trigger timeout=0 s repeat measurement=0 times, repeat focus=No. The following dispersion conditions are set: Name 3.0 bar, dispersing type=RODOS injector=4 mm, with=0 cascade elements, primary pressure=3.0 bar, feeder type=ROTARY, Rotation: 18%, check prim. Pres before measurement=No vacuum extraction type=Nilfisk, delay=2 s.

An adequate amount of approximately 1.0 g of the sample is weighed and filled into the groove in the rotary feeder. This is then blown by compressed air via the RODOS dry powder disperser through the measuring zone triggering a measurement. The sample particle size is measured and the $D_{90}$[D(v,0.9)], $D_{50}$[D(v,0.5)], $D_{10}$[D(v,0.1)] and Span recorded.

See J. P. Mitchell and M. W. Nagel in "Particle size analysis of aerosols from medicinal inhalers" KONA No. 2004, 22, 32 for further details concerning the measurement of particles sizes. The appropriate particle size may also be provided by the lyophilisation process described hereinabove although further micronisation may be performed by grinding in a mill, e.g. an air jet, ball or vibrator mill, by sieving, by crystallization, by spray-drying or by further lyophilisation.

The formulation of the present invention also contains an α-lactose monohydrate carrier. Such carriers are termed "coarse" carriers to distinguish them from fine particles which are entrained into the lung. They are well known in the art and are readily available commercially from a number of sources. A coarse carrier usually contains some fine particles of the same material (inherently present and/or deliberately added). Such fine particles assist with the release of the active ingredient(s) from the coarse carrier.

In general, the particle size of the α-lactose monohydrate carrier should be such that it can be entrained in an air stream but not deposited in the key target sites of the lung. Accordingly, the α-lactose monohydrate preferably has a mean particle size of 40 microns or more, more preferably the α-lactose monohydrate particles have a volume mean diameter (VMD) of 50-250 microns.

Preferably substantially all particles of the α-lactose monohydrate batches are less than 300 μm in size.

It is more preferable, that the particle size distribution of the α-lactose monohydrate fraction is d10=10-25 μm, d50=85-105 μm, d90=140-180 μm, NLT99%<300 μm and 1.5-8.5%<10 μm, or d10=19-43 μm, d50=50-65 μm, d90=75-106 μm, NLT99%<300 μm and 1.5-2-5%<10 μm.

The α-lactose monohydrate may contain inherent fine content (i.e. fine lactose). Such lactose has a particle size less than 10 μm in size, more likely 1-5 μm.

Fine α-lactose monohydrate are particles that are inherently present and contained within the α-lactose monohydrate carrier (as received from a commercial supplier). Such fine particles typically have a particle size of less than 10 μm in size, more likely 1-5 μm. MMAD of the inherent fines may be measured using a next generation impactor (NGI). Fine particles of same material as the α-lactose monohydrate carrier may also be deliberately added to the formulation. They are not considered to be a ternary agent because they do not introduce a third substance beyond the active and the carrier particles.

Preferably, the particle size distribution of the ternary excipient is d10=0.5-6.0 μm, d50=7.0-12.0 μm, d90=15.0-30.0 μm and NLT99%<10 μm.

The particle size distribution of the lactose provided herein may be measured by laser diffraction as a dry dispersion in air, e.g. with a Sympatec HELOS/BF equipped with a RODOS disperser and a VIBRI feeder unit. In particular, lens type R5: 0.5/4.5 . . . 875 μm is used. The following information is set on the equipment: density=1.5500 g/cm$^3$; shape factor=1.00, calculation mode=HRLD, forced stability=0. The following trigger conditions are set: Name=CH12, 0.2%, reference duration=10 s (single), time base=100 ms, focus prior to measurement=yes, normal measurement=standard mode, start=0.000 s, channel 12≥0.2%, valid=always, stop after=5.000 s, channel 12≤0.2%, or after=60.000 s, real time, repeat measurement=0, repeat focus=No. The following dispersion conditions are set: Name 1.5 bar; 85%; 2.5 mm, dispersing type=RODOS/M, injector=4 mm, with=0 cascade elements, primary pressure=1.5 bar, always auto adjust before ref. meas.=No, feeder type=VIBRI, feed rate=85%, gap width=2.5 mm, funnel rotation=0%, cleaning time=10 s, use VIBRI Control=No, vacuum extraction type=Nilfisk, delay=5 s. An adequate amount of approximately 5 g of the sample is transferred into a weighing paper using a clean dry stainless steel spatula and then poured into the funnel on the VIBRI chute. The sample is measured. The pressure is maintained at about 1.4-1.6 bar, measurement time=1.0-10.0 seconds, $C_{opt}$=5-15% and vacuum < or =7 mbar. The procedure is repeated two more times.

Alternatively, the particle size distribution of the lactose may be measured by laser diffraction as a dry dispersion, e.g. using a Sympatec HELOS/BF equipped with a RODOS, RODOS/M or OASIS/M disperser and a VIBRI feeder unit. In particular, lens type R4: 0.5/4.5 . . . 350 μm is used. The following information is set on the equipment: density=1.550 g/cm$^3$; shape factor=1.00, calculation mode=HRLD, forced stability=0. The following trigger conditions are set: Name=Optical Concentration >0.5%, reference duration=4 s (single), time base=100 ms, focus prior to measurement=yes, normal measurement=standard mode, start=0.000 s, Optical Concentration > or =0.5%, valid=0.5%< or =Channel 9< or =99.0%, stop after=1 s Optical Concentration <0.5%, or after=20.000 s, real time, trigger timeout=0 s repeat measurement=0 times, repeat focus=No. The following dispersion conditions are set: Name 1.5 bar; 75%; 1.8 mm, dispersing type=RODOS/M, injector=4 mm, with=0 cascade elements, primary pressure=1.5 bar, always auto adjust before ref. meas.=No, feeder type=VIBRI, feed rate=75%, gap width=1.8 mm, funnel rotation=0%, cleaning time=10 s, use VIBRI Control=No, vacuum extraction type=Nilfisk, delay=5 s. An adequate amount of approximately 5 g of the sample is weighed and then poured into the funnel on the VIBRI chute. This is then blown by compressed air via the RODOS dry powder disperser through the measuring zone triggering a measurement. The sample particle size is measured.

Dry powder inhalable formulations may also contain a ternary excipient. Ternary excipients are well-known in the art and are used to provide additional stability to the active ingredients. Typically the additional stability is provided by reducing the amount of water adsorption and by promoting release of the active ingredient from the coarse carrier particles.

Ternary excipients are also known as force control agents, lubricants or anti-adherents. They use the term "ternary" because they add a third material to the formulation over the active ingredient(s) and the carrier. It should be noted that the coarse carrier (i.e. α-lactose monohydrate) usually contains some fine particles of the same material (inherently present and/or deliberately added). Such fine particles composed of the same material as the coarse carrier are not ternary excipients.

As the present invention provides an improvement in stability for fluticasone propionate over the mono-product, a ternary excipient is not an essential feature for enhancing stability. However, it may be added to provide further enhancement in the stability and powder flowability of the fluticasone propionate and to achieve a higher fine particle fraction.

Accordingly, the present invention provides two distinct embodiments. In one embodiment, the dry powder inhalable formulation of the present invention does not include a ternary excipient. For example, the formulation may consist of fluticasone propionate, albuterol sulfate, and α-lactose monohydrate (an α-lactose monohydrate carrier, optionally containing fine α-lactose monohydrate particles).

In another embodiment, the dry powder inhalable formulation of the present invention further comprises a ternary excipient.

Typical examples of ternary excipients which may be formulated within the formulation of the present invention include metal stearates (such as magnesium and calcium stearate), fatty acids (e.g. stearic acid), amino acids (such as leucine) and phospholipids (such as lecithin).

It is preferred wherein the ternary excipient formulated within the formulation of the present invention is magnesium stearate. It is also preferred wherein the proportion of magnesium stearate contained within the formulation is from 0.01-3.0% by weight of the formulation.

Ternary excipients can be used to provide additional stability.

The formulation of the present invention is preferably prepared by mixing fluticasone propionate, albuterol sulfate and α-lactose monohydrate to form the formulation.

Preferably the formulation of the present invention is prepared by mixing (in any order) fluticasone propionate, albuterol sulfate and α-lactose monohydrate to form the formulation.

The formulation of the present invention is preferably prepared by separately mixing fluticasone propionate and α-lactose monohydrate, and albuterol sulfate and α-lactose monohydrate, and combining the mixtures to form the formulation.

More specifically, the dry powder inhalable formulation according to the present invention is prepared using a process comprising the steps of:
(i) preparing a mixture of fluticasone propionate and α-lactose monohydrate to form a first blend;
(ii) preparing a mixture of albuterol sulfate and α-lactose monohydrate to form a second blend; and
(iii) mixing the first blend and the second blend to form the formulation.

The present invention also provides a product obtainable by this process.

Even more specifically, the dry powder inhalable formulation according to the present invention is prepared using a process comprising the steps of:
(i) preparing a mixture of fluticasone propionate and α-lactose monohydrate to form a first blend;
(ii) preparing a mixture of albuterol sulfate and α-lactose monohydrate to form a second blend;
(iii) mixing the first blend and the second blend to form the formulation; and
(iv) conditioning the formulation.

Where the process includes the step of conditioning the formulation, the step includes exposure of the formulation to humid conditions. Typically the humid conditions are 65% relative humidity (RH) at a temperature of 30° C.

Preferably, conditioning the formulation includes exposure of the formulation to 65% RH/30° C. for a duration of 21 to 36 days. More preferably, conditioning the formulation includes exposure of the formulation to 65% RH/30° C. for a duration of 28 to 35 days. Most preferably, conditioning the formulation includes exposure of the formulation to 65% RH/30° C. for a duration of 28 days.

Preferably, the formulation is loaded into a formulation reservoir of a dry powder inhaler, and the dry powder inhaler is placed on a tray prior to the performance of step (iv).

Alternatively, the formulation is loaded into a formulation reservoir of a dry powder inhaler, and the dry powder inhaler is placed on a tray and the inhaler and tray are wrapped with a polyethylene wrap prior to the performance of step (iv).

Preferably, the inhaler and the tray are left unwrapped during the conditioning process.

The tray may be agitated during the conditioning process (with the principle aim to ensure that all of the formulation particles contained within the inhaler are equally exposed to the humid atmosphere). The agitating also helps to avoid or reduce agglomeration of the particles during the conditioning process.

The present invention also provides a product obtainable by this process.

The present invention also provides a process for preparing a dry powder inhalable formulation, comprising the steps of:
(i) preparing a mixture of fluticasone propionate, albuterol sulfate and α-lactose monohydrate; and
(ii) conditioning the mixture.

Preferably, conditioning the formulation includes exposure of the formulation to 65% RH/30° C. for a duration of 21 to 36 days. More preferably, conditioning the formulation includes exposure of the formulation to 65% RH/30° C. for a duration of 28 to 35 days. Most preferably, conditioning the formulation includes exposure of the formulation to 65% RH/30° C. for a duration of 28 days.

Preferably, the formulation is loaded into a formulation reservoir of a dry powder inhaler, and the dry powder inhaler is placed on a tray prior to the performance of step (ii).

Alternatively, the formulation is loaded into a formulation reservoir of a dry powder inhaler, and the dry powder inhaler is placed on a tray and the inhaler and tray are wrapped with a polyethylene wrap prior to the performance of step (iv).

Preferably, the inhaler and the tray are left unwrapped during the conditioning process.

The tray may be agitated during the conditioning process (with the principle aim to ensure that all of the formulation particles contained within the inhaler are equally exposed to the humid atmosphere). The agitating also helps to avoid or reduce agglomeration of the particles during the conditioning process.

The present invention also provides a product obtainable by this process.

Where a ternary excipient is included in the formulation, it is most preferred that the ternary excipient is added to α-lactose monohydrate prior to dispensing the lactose for use in preparing the first and second blends.

Accordingly, a dry powder inhalable formulation comprising fluticasone propionate, albuterol sulfate and α-lactose monohydrate is obtainable by the processes disclosed herein.

Powder mixing is an important consideration in providing a dry powder inhalable formulation, insofar as the mixing conditions and apparatus can directly influence aerosolisation performance. This is because the ability of a dry powder formulation to work effectively is dependent not only on the formation of an adhesive mixture, but also on the liberation and distribution of the drug from and onto the carrier, respectively.

Unlike fluid mixing, wherein the mixing of two components is governed simply by a concentration gradient, powder particles require an input of energy (i.e. kinetic energy) to facilitate mixing. Therefore, a powder mixing apparatus is required to induce motion either by rotational/translational movement of a container in which the powder or formulation is contained, or alternatively the powder or formulation is moved by contact with an impeller or chopper that is contained within the powder mixing vessel.

Two mixing techniques specific to dry powder inhaler technology can be applied. These mixing techniques are based upon tumbling mixers (sometimes referred to as "blenders") (e.g. Turbula® and V-blenders) which are used for low-speed mixing, and high-speed mixers (e.g. Pharma-Connect®) which use a mixing arm (e.g. an impeller or chopper or combination thereof).

A low-speed tumbling mixer container is typically mounted within a frame upon a mixing apparatus. The container is supported so that it can be rotated about an axis. In operation, the tumbling action creates circular mixing zones and paths within the container. Thus, tumbling mixers mix powder under the force of gravity as the mixer tumbles (i.e. rotates). The interactions of the powder particles with each other and against the walls of the mixer cause shear mixing to occur. The strength of the shear force experienced by a powder or substrate within a mixture is dependent upon the speed of mixing.

A high-speed mixer typically comprises a container having a mixing arm within the container. Typically a mixing arm is an impeller blade or a chopper blade or a combination thereof. Impeller blades are typically centrally mounted within the mixer at the bottom of the container. Chopper blades are typically located on the side wall of the mixing container. In operation, the mixing arm directly contacts the particles of active ingredient and coarse carrier, and imparts force into the powder. In doing so, the mixing arm throws powder from the centre of the mixing bowl towards the wall by centrifugal force. The powder is then forced upwards before resting back towards the centre of the mixing arm. This pattern of particulate movement tends to mix the powders quickly owing to high shear forces generated by the high-speed mixing arm directly contacting with powder particles.

The principles of shear mixing are known within the common general knowledge, and for example are discussed in Aulton's Pharmaceutics: The Design and Manufacture of Medicines, M. E. Aulton, Philadelphia, Elsevier Limited, 2007.

The formulation of the present invention is for use in the treatment of asthma or COPD. It may be for use in the long-term treatment of asthma and/or COPD and the treatment of acute exacerbations of asthma and/or COPD, wherein the formulation is administered as a maintenance dose for the long-term treatment of asthma and pro re nata (p.r.n.) as a rescue medication for the treatment of acute exacerbations of asthma.

Preferably, the formulation of the present invention is for use in the treatment of asthma. It may be for use in the long-term treatment of asthma and the treatment of acute exacerbations of asthma and, wherein the formulation is administered as a maintenance dose for the long-term treatment of asthma and pro re nata (p.r.n.) as a rescue medication for the treatment of acute exacerbations of asthma.

Preferably the formulation of the present invention is for use in the treatment of asthma in patients with step 2 asthma as defined by the Global Initiative for Asthma (GINA) 2005 guidelines. Such patients are considered to be suffering from mild persistent asthma. Step 2 is also defined by reference to a patient's airflow limitation based on measurement of peak flow volume (PEF) or forced expiratory volume in one second ($FEV_1$) (typically $FEV_1$ and PEF are measured after administration of an adequate dose of at least one short-acting inhaled bronchodilator in order to minimise the variability of measurements).

Patients suffering from step 2 asthma defined by GINA have airflow limitations of PEF or $FEV_1$ of ≥80% of predicted and a PEF variability of 20-30%.

Patients suffering from step 2 asthma defined by GINA also experience daily symptoms greater than once a week but less than once a day.

Patients suffering from step 2 asthma defined by GINA also experience night-time symptoms greater than two times a month but not greater than once a week.

Preferably the formulation of the present invention is for use in the treatment of COPD in patients with airflow limitation severity GOLD 2 as defined by the committee for the Global Initiative for Chronic Obstructive Lung Disease (GOLD) 2017 guidelines. Such patients are considered to be suffering from moderate COPD. GOLD 2 is also defined by reference to a patient's airflow limitation based on measurement of $FEV_1$ post-bronchodilator administration (typically $FEV_1$ of patients is measured after administration of an adequate dose of at least one short-acting inhaled bronchodilator in order to minimise the variability of measurements). Patient's suffering from GOLD 2 defined COPD have airflow limitations of 50%≤$FEV_1$<80% predicted.

There is also provided the use of fluticasone propionate, albuterol sulfate and an α-lactose monohydrate carrier for the preparation of a formulation for the treatment of asthma or COPD. Also provided is a method for treating asthma or COPD comprising administering an effective amount of a dry powder inhalable formulation comprising fluticasone propionate, albuterol sulfate and an α-lactose monohydrate carrier to a patient in need thereof. The treatment may be the long-term treatment of asthma and/or COPD and the treatment of acute exacerbations of asthma and/or COPD, wherein the formulation is administered as a maintenance dose for the long-term treatment of asthma and pro re nata (p.r.n.) as a rescue medication for the treatment of acute exacerbations of asthma.

The formulation provided by the present invention is based upon a combined treatment of fluticasone propionate and albuterol sulfate in a single formulation, which allows patients to receive the benefits of daily maintenance medication and rescue therapy contained within one prescribed dosage (termed a "fixed-dose combination" or "FDC"). Should the patient's symptoms deteriorate (upon experiencing an exacerbation) they will then use the same device as a rescue medication, following secondary (frequency indicating) dosage instructions. Upon multiple actuations of the device, the patient obtains an increased dosage of albuterol sulfate that in turn induces bronchodilation and hence provides symptomatic relief and concomitantly provides an increased dose of inhaled corticosteroid to address inflammation that may underlie the worsening of symptoms. Furthermore, this approach serves to improve patient convenience and compliance through unifying a multi-faceted treatment into a single device. First, the present invention conveniently provides patients with one inhaler to carry, as opposed to two separate inhalers that each contains a different active ingredient. Secondly, patient compliance is directly addressed and improved, in that, when used as a rescue medication, the patient not only experiences relief from receiving albuterol sulfate but also receives an additional dose of fluticasone propionate. This feature of the invention is particularly important and beneficial in circumstances where the patient has missed a maintenance dose.

Preferably the total administered daily dose of fluticasone propionate does not exceed 1,000 µg, and wherein the total administered daily dose of albuterol sulfate does not exceed 800 µg. Preferred values are fluticasone propionate 55 or and 30 µg, and albuterol sulfate 90 µg, per actuation based on the metered dose of each active ingredient.

The present invention also provides the use of albuterol sulfate to stabilise fluticasone propionate in a dry powder inhalation formulation. That is albuterol sulfate interacts with fluticasone propionate and maintains the particle size distribution of the fluticasone propionate over time (i.e. the physical stability of the fluticasone propionate).

The dry powder formulation may be metered and filled into capsules, e.g. gelatin or hydroxypropyl methylcellulose capsules, such that the capsule contains a unit dose of active ingredient. When the dry powder is in a capsule containing a unit dose of active ingredient, the total amount of composition will depend on the size of the capsules and the characteristics of the inhalation device with which the capsules are being used. However, typical examples of total fill weights of dry powder per capsule are 1-25 mg. Alternatively, the dry powder composition according to the invention may be filled into the reservoir of a multi-dose dry powder inhaler (MDPI).

Preferably, the multi-dose dry powder inhaler includes a cyclone deagglomerator for breaking up agglomerates of the active ingredients and carrier. This occurs prior to inhalation of the powder by a patient. The deagglomerator includes an inner wall defining a swirl chamber extending along an axis from a first end to a second end, a dry powder supply port, an inlet port, and an outlet port.

The supply port is in the first end of the swirl chamber for providing fluid communication between a dry powder delivery passageway of the inhaler and the first end of the swirl chamber. The inlet port is in the inner wall of the swirl chamber adjacent to the first end of the swirl chamber and provides fluid communication between a region exterior to the deagglomerator and the swirl chamber. The outlet port provides fluid communication between the second end of the swirl chamber and a region exterior to the deagglomerator.

A breath induced low pressure at the outlet port causes air flows into the swirl chamber through the dry powder supply port and the inlet port. The air flows collide with each other and with the wall of the swirl chamber prior to exiting through the outlet port, such that the active is detached from the carrier (lactose). The deagglomerator further includes vanes at the first end of the swirl chamber for creating additional collisions and impacts of entrained powder.

A first breath-actuated air flow is directed for entraining a dry powder from an inhaler into a first end of a chamber extending longitudinally between the first end and a second end, the first air flow directed in a longitudinal direction.

A second breath-actuated airflow is directed in a substantially transverse direction into the first end of the chamber such that the air flows collide and substantially combine.

Then, a portion of the combined air flows is deflected in a substantially longitudinal direction towards a second end of the chamber, and a remaining portion of the combined air flows is directed in a spiral path towards the second end of the chamber. All the combined air flows and any dry powder entrained therein are then delivered from the second end of the chamber to a patient's mouth.

The deagglomerator ensures that particles of the actives are small enough for adequate penetration of the powder into a bronchial region of a patient's lungs during inhalation by the patient.

Thus, preferably, where the dry powder formulation of the present invention is used in conjunction with a multi-dose dry powder inhaler device, the deagglomerator of the inhaler device comprises: an inner wall defining a swirl chamber extending along an axis from a first end to a second end; a dry powder supply port in the first end of the swirl chamber for providing fluid communication between a dry powder delivery passageway of the inhaler and the first end of the swirl chamber; at least one inlet port in the inner wall of the swirl chamber adjacent to the first end of the swirl chamber providing fluid communication between a region exterior to the deagglomerator and the first end of the swirl chamber; an outlet port providing fluid communication between the second end of the swirl chamber and a region exterior to the deagglomerator; and vanes at the first end of the swirl chamber extending at least in part radially outwardly from the axis of the chamber, each of the vanes having an oblique surface facing at least in part in a direction transverse to the axis; whereby a breath induced low pressure at the outlet port causes air flows into the swirl chamber through the dry powder supply port and the inlet port.

The inhaler preferably has a reservoir for containing the formulation and an arrangement for delivering a metered dose of the formulation from the reservoir. The reservoir is typically a pressure system. The inhaler preferably includes: a sealed reservoir including a dispensing port; a channel communicating with the dispensing port and including a pressure relief port; a conduit providing fluid communication between an interior of the sealed reservoir and the pressure relief port of the channel; and a cup assembly movably received in the channel and including, a recess adapted to receive formulation when aligned with the dispensing port, a first sealing surface adapted to seal the dispensing port when the recess is unaligned with the dispensing port, and a second sealing surface adapted to sealing the pressure relief port when the recess is aligned with the dispensing port and unseal the pressure relief port when the recess is unaligned with the dispensing port.

The inhaler preferably has a dose counter. The inhaler includes a mouthpiece for patient inhalation, a dose-metering arrangement including a pawl movable along a predetermined path during the metering of a dose of formulation to the mouthpiece by the dose-metering arrangement, and a dose counter.

In a preferred form, the dose counter includes a bobbin, a rotatable spool, and a rolled ribbon received on the bobbin, rotatable about an axis of the bobbin. The ribbon has indicia thereon successively extending between a first end of the ribbon secured to the spool and a second end of the ribbon positioned on the bobbin. The dose counter also includes teeth extending radially outwardly from the spool into the predetermined path of the pawl so that the spool is rotated by the pawl and the ribbon advanced onto the spool during the metering of a dose to the mouthpiece.

The preferred inhaler includes a simple, accurate and consistent mechanical dose metering system that dispenses dry powdered formulation in discrete amounts or doses for patient inhalation, a reservoir pressure system that ensures consistently dispensed doses, and a dose counter indicating the number of doses remaining in the inhaler.

The inhaler 10 generally includes a housing 18, and an assembly 12 received in the housing (see FIG. 2). The housing 18 includes a case 20 having an open end 22 and a mouthpiece 24 for patient inhalation, a cap 26 secured to and closing the open end 22 of the case 20, and a cover 28 pivotally mounted to the case 20 for covering the mouthpiece 24 (see FIGS. 1, 2 and 9). The housing 18 is preferably manufactured from a plastic such as polypropylene, acetal or moulded polystyrene, but may be manufactured from metal or another suitable material.

The internal assembly 12 includes a reservoir 14 for containing dry powered formulation in bulk form, a deagglomerator 10' that breaks down the formulation between a delivery passageway 34 and the mouthpiece 24, and a spacer 38 connecting the reservoir to the deagglomerator.

The reservoir 14 is generally made up of a collapsible bellows 40 and a hopper 42 having an dispenser port 44 (see FIGS. 2-5 and 7-8) for dispensing formulation upon the bellows 40 being at least partially collapsed to reduce the internal volume of the reservoir.

The hopper 42 is for holding the dry powder formulation in bulk form and has an open end 46 closed by the flexible accordion-like bellows 40 in a substantially air-tight manner.

An air filter 48 covers the open end 46 of the hopper 42 and prevents dry powder formulation from leaking from the hopper 42 (see FIG. 7).

A base 50 of the hopper 42 is secured to a spacer 38, which is in turn secured to the deagglomerator 10' (see FIGS. 3-5 and 7-8). The hopper 42, the spacer 38, and the deagglomerator 10' are preferably manufactured from a plastic such as polypropylene, acetal or moulded polystyrene, but may be manufactured from metal or another suitable material.

The hopper 42, the spacer 38 and the deagglomerator 10' are connected in a manner that provides an air tight seal between the parts. For this purpose heat or cold sealing, laser welding or ultrasonic welding could be used, for example.

The spacer 38 and the hopper 42 together define the formulation delivery passageway 34, which preferably includes a venturi 36 (see FIG. 16) for creating an entraining air flow. The spacer 38 defines a slide channel 52 communicating with the dispenser port 44 of the hopper 42, and a chimney 54 providing fluid communication between the formulation delivery passageway 34 and a supply port 22' of the deagglomerator 10' (see FIGS. 7 and 8). The slide channel 52 extends generally normal with respect to the axis "A" of the inhaler 10.

The deagglomerator 10' breaks down agglomerates of dry powder formulation before the dry powder leaves the inhaler 10 through the mouthpiece 24.

Referring to FIGS. 17 to 22, the deagglomerator 10' breaks down agglomerates of formulation, or formulation and carrier, before inhalation of the formulation by a patient.

In general, the deagglomerator 10' includes an inner wall 12' defining a swirl chamber 14' extending along an axis A' from a first end 18' to a second end 20'. The swirl chamber 14' includes circular cross-sectional areas arranged transverse to the axis A', that decrease from the first end 18' to the second end 20' of the swirl chamber 14', such that any air flow traveling from the first end of the swirl chamber to the second end will be constricted and at least in part collide with the inner wall 12' of the chamber.

Preferably, the cross-sectional areas of the swirl chamber 14' decrease monotonically. In addition, the inner wall 12' is preferably convex, i.e., arches inwardly towards the axis A', as shown best in FIG. 22.

As shown in FIGS. 17, 19 and 22, the deagglomerator 10' also includes a dry powder supply port 22' in the first end 18' of the swirl chamber 14' for providing fluid communication between a dry powder delivery passageway of an inhaler and the first end 18' of the swirl chamber 14'. Preferably, the dry powder supply port 22' faces in a direction substantially parallel with the axis A' such that an air flow, illustrated by arrow 1' in FIG. 22, entering the chamber 14' through the supply port 22' is at least initially directed parallel with respect to the axis A' of the chamber.

Referring to FIGS. 17 to 22, the deagglomerator 10' additionally includes at least one inlet port 24' in the inner wall 12' of the swirl chamber 14' adjacent to or near the first end 18' of the chamber providing fluid communication between a region exterior to the deagglomerator and the first end 18' of the swirl chamber 14'. Preferably, the at least one inlet port comprises two diametrically opposed inlet ports 24', 25' that extend in a direction substantially transverse to the axis A' and substantially tangential to the circular cross-section of the swirl chamber 14'. As a result, air flows, illustrated by arrows 2' and 3' in FIGS. 17 and 21, entering the chamber 14' through the inlet ports are at least initially directed transverse with respect to the axis A' of the chamber and collide with the air flow 1' entering through the supply port 22' to create turbulence. The combined air flows, illustrated by arrow 4' in FIGS. 21 and 22, then collide with the inner wall 12' of the chamber 14', form a vortex, and create additional turbulence as they move towards the second end 20' of the chamber.

Referring to FIGS. 17-19 and 22, the deagglomerator 10' includes vanes 26' at the first end 18' of the swirl chamber 14' extending at least in part radially outwardly from the axis A' of the chamber. Each of the vanes 26' has an oblique surface 28' facing at least in part in a direction transverse to the axis A' of the chamber. The vanes 26' are sized such that at least a portion 4A' of the combined air flows 4' collide with the oblique surfaces 28', as shown in FIG. 22. Preferably, the vanes comprise four vanes 26', each extending between a hub 30' aligned with the axis A' and the wall 12' of the swirl chamber 14'.

As shown in FIGS. 17 to 22, the deagglomerator 10' further includes an outlet port 32' providing fluid communication between the second end 20' of the swirl chamber 14' and a region exterior to the deagglomerator. A breath induced low pressure at the outlet port 32' causes the air flow 1' through the supply port 22' and the air flows 2',3' through the inlet ports and draws the combined air flow 4' through the swirl chamber 14'. The combined air flow 4' then exits the deagglomerator through the outlet port 32'. Preferably the outlet port 32' extends substantially transverse to the axis A', such that the air flow 4' will collide with an inner wall of the outlet port 32' and create further turbulence.

During use of the deagglomerator 10' in combination with the inhaler, patient inhalation at the outlet port 32' causes air flows 1',2',3' to enter through, respectively, the dry powder supply port 22' and the inlet ports. Although not shown, the air flow 1' through the supply port 22' entrains the dry powder into the swirl chamber 14'. The air flow 1' and entrained dry powder are directed by the supply port 22' into the chamber in a longitudinal direction, while the air flows 2',3' from the inlet ports are directed in a transverse direction, such that the air flows collide and substantial combine.

A portion of the combined air flow 4' and the entrained dry powder then collide with the oblique surfaces 28' of the vanes 26' causing particles and any agglomerates of the dry powder to impact against the oblique surfaces and collide with each other. The geometry of the swirl chamber 14' causes the combined air flow 4' and the entrained dry powder to follow a turbulent, spiral path, or vortex, through the chamber. As will be appreciated, the decreasing cross-sections of the swirl chamber 14' continuously changes the direction and increases the velocity of the spiralling combined air flow 4' and entrained dry powder. Thus, particles and any agglomerates of the dry powder constantly impact against the wall 12' of the swirl chamber 14' and collide with each other, resulting in a mutual grinding or shattering action between the particles and agglomerates. In addition, particles and agglomerates deflected off the oblique surfaces 28' of the vanes 26' cause further impacts and collisions.

Upon exiting the swirl chamber 14', the direction of the combined air flow 4 and the entrained dry powder is again changed to a transverse direction with respect to the axis A', through the outlet port 32'. The combined air flow 4' and the entrained dry powder retain a swirl component of the flow, such that the air flow 4' and the entrained dry powder spirally swirls through the outlet port 32'. The swirling flow causes additional impacts in the outlet port 32' so as to result in further breaking up of any remaining agglomerates prior to being inhaled by a patient.

As shown in FIGS. 17 to 22, the deagglomerator is preferably assembly from two pieces: a cup-like base 40' and a cover 42'. The base 40' and the cover 42' are connected to form the swirl chamber 14'. The cup-like base 40' includes the wall 12' and the second end 20' of the chamber and defines the outlet port 32'. The base 40' also includes the inlet ports of the swirl chamber 14'. The cover 42' forms the vanes 26' and defines the supply port 22'.

The base 40' and the cover 42' of the deagglomerator are preferably manufactured from a plastic such as polypropylene, acetal or moulded polystyrene, but may be manufactured from metal or another suitable material. Preferably, the cover 42' includes an anti-static additive, so that dry powder will not cling to the vanes 26'. The base 40' and the cover 42' are then connected in a manner that provides an air tight seal between the parts. For this purpose heat or cold sealing, laser welding or ultra-sonic welding could be used, for example.

Although the inhaler 10 is shown with a particular deagglomerator 10', the inhaler 10 is not limited to use with the deagglomerator shown and can be used with other types of deagglomerators or a simple swirl chamber.

The dose metering system includes a first yoke 66 and a second yoke 68 mounted on the internal assembly 12 within the housing 18, and movable in a linear direction parallel with an axis "A" of the inhaler 10 (see FIG. 2). An actuation spring 69 is positioned between the cap 26 of the housing 18 and the first yoke 66 for biasing the yokes in a first direction towards the mouthpiece 24. In particular, the actuation spring 69 biases the first yoke 66 against the bellows 40 and the second yoke 68 against cams 70 mounted on the mouthpiece cover 28 (see FIG. 9).

The first yoke 66 includes an opening 72 that receives and retains a crown 74 of the bellows 40 such that the first yoke 66 pulls and expands the bellows 40 when moved towards the cap 26, i.e., against the actuation spring 69 (see FIG. 2). The second yoke 68 includes a belt 76, which receives the first yoke 66, and two cam followers 78 extending from the belt in a direction opposite the first yoke 66 (see FIGS. 3, 11 and 12), towards the cams 70 of the mouthpiece cover 28 (FIGS. 9,10).

The dose metering system also includes the two cams 70 mounted on the mouthpiece cover 28 (see FIGS. 9 and 10), and movable with the cover 28 between open and closed positions. The cams 70 each include an opening 80 for allowing outwardly extending hinges 82 of the case 20 to pass there through and be received in first recesses 84 of the cover 28. The cams 70 also include bosses 86 extending outwardly and received in second recesses 88 of the cover 28, such that the cover 28 pivots about the hinges 82 and the cams 70 move with the cover 28 about the hinges.

Each cam 70 also includes first, second and third cam surfaces 90,92,94, and the cam followers 78 of the second yoke 68 are biased against the cam surfaces by the actuation spring 69. The cam surfaces 90,92,94 are arranged such the cam followers 78 successively engage the first cam surfaces 90 when the cover 28 is closed, the second cam surfaces 92 when the cover 28 is partially opened, and the third cam surfaces 94 when the cover 28 is fully opened. The first cam surfaces 90 are spaced further from the hinges 82 than the second and the third cam surfaces, while the second cam surfaces 92 are spaced further from the hinges 82 than the third cam surfaces 94. The cams 70, therefore, allow the yokes 66,68 to be moved by the actuation spring 69 parallel with the axis "A" of the inhaler 10 in the first direction (towards the mouthpiece 24) through first, second and third positions as the cover 28 is opened. The cams 70 also push the yokes 66, 68 in a second direction parallel with the axis "A" (against the actuation spring 69 and towards the cap 26 of the housing 18) through the third, the second and the first positions as the cover 28 is closed.

The dose metering system further includes a cup assembly 96 movable between the dispenser port 44 of the reservoir 14 and the delivery passageway 34. The cup assembly 96 includes a formulation cup 98 mounted in a sled 100 slidably received in the slide channel 52 of the spacer 38 below the hopper 42 (see FIGS. 5 and 6). The formulation cup 98 includes a recess 102 adapted to receive formulation from the dispenser port 44 of the reservoir 14 and sized to hold a predetermined dose of dry powdered formulation when filled. The cup sled 100 is biased along the slide channel 52 from the dispenser port 44 of the hopper 42 towards the delivery passageway 34 by a cup spring 104, which is secured on the hopper 42 (see FIGS. 4 and 5).

Figure 3:
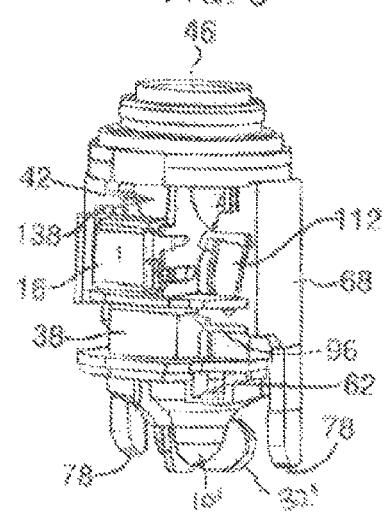
FIG. 3 is a second side isometric view of a main assembly of the inhaler of FIG. 1.
Figure 4:
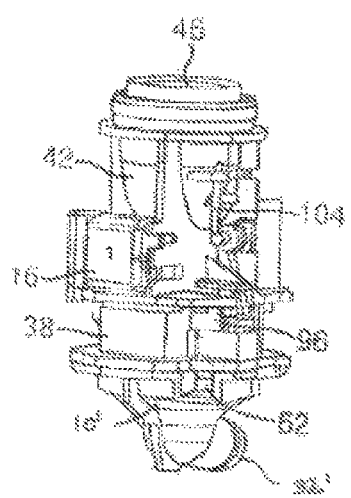
FIG. 4 is a second side isometric view of the main assembly of the inhaler of FIG. 1, shown with a yoke removed.
Figure 5:
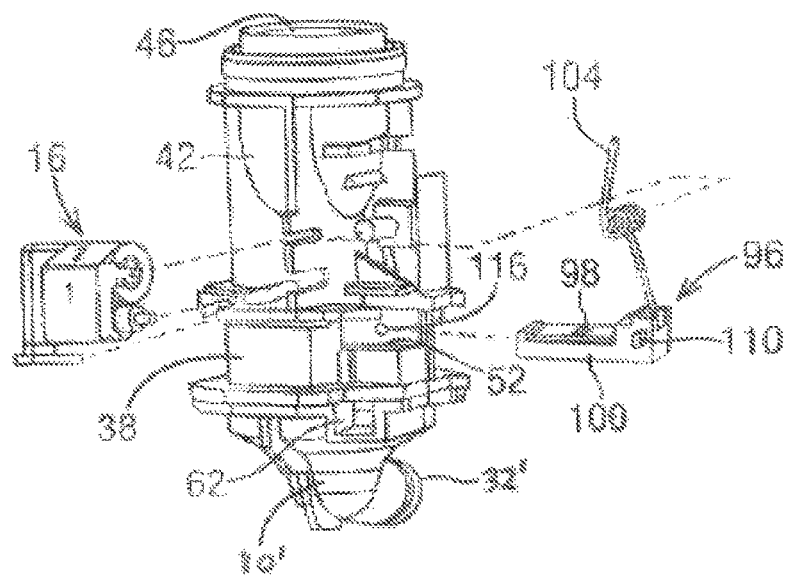
FIG. 5 is an exploded first side isometric view of the main assembly of the inhaler of FIG. 1.
Figure 11:
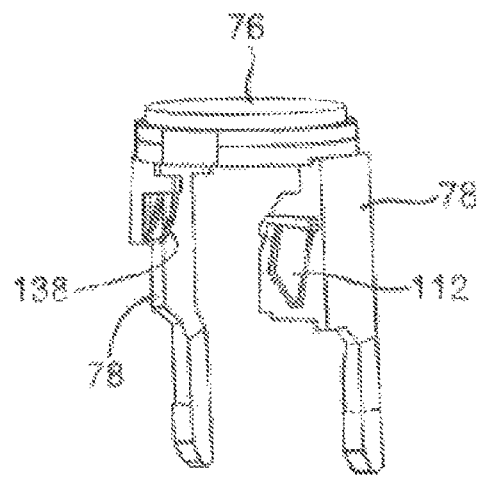
FIG. 11 is a second side isometric view of the yoke of the inhaler of FIG. 1.
Figure 12:
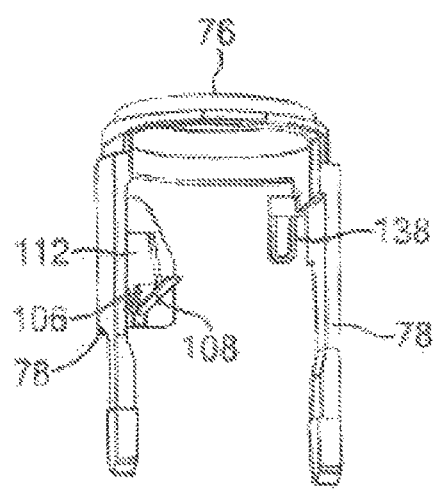
FIG. 12 is a first side isometric view of the yoke of the inhaler of FIG. 1, showing a ratchet and a push bar of the yoke.

The dose metering system also includes a ratchet 106 and a push bar 108 on one of the cam followers 78 of the second yoke 68 that engage a boss 110 of the cup sled 100 (see FIGS. 5,11 and 12). The ratchet 106 is mounted on a flexible flap 112 and is shaped to allow the boss 110 of the sled 100 to depress and pass over the ratchet 106, when the boss 110 is engaged by the push bar 108. Operation of the dose metering system is discussed below.

The reservoir pressure system includes a pressure relief conduit 114 in fluid communication with the interior of the reservoir 14 (see FIGS. 7 and 8), and a pressure relief port 116 in a wall of the slide channel 52 (see FIGS. 5 and 8) providing fluid communication with the pressure relief conduit 114 of the hopper 42.

Figure 6:
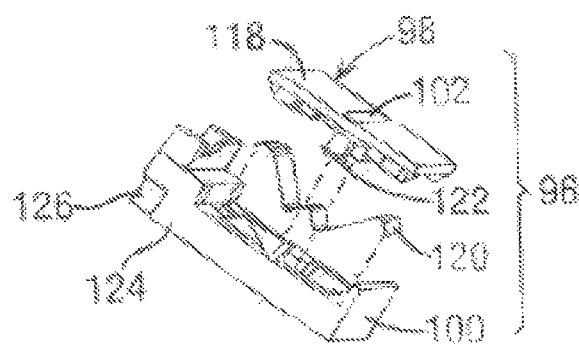
FIG. 6 is an exploded enlarged isometric view of a formulation cup of the inhaler of FIG. 1.

The formulation cup assembly 96 includes a first sealing surface 118 adapted to seal the dispenser port 44 upon the cup assembly being moved to the delivery passageway 34 (see FIGS. 5 and 6). A sealing spring 120 is provided between the sled 100 and the cup 98 for biasing the formulation cup 98 against a bottom surface of the hopper 42 to seal the dispenser port 44 of the reservoir 14. The cup 98 includes clips 122 that allow the cup to be biased against the reservoir, yet retain the cup in the sled 100.

The sled 100 includes a second sealing surface 124 adapted to seal the pressure relief port 116 when the recess 102 of the cup 98 is aligned with the dispenser port 44, and an indentation 126 (see FIG. 6) adapted to unseal the pressure relief port 116 when the first sealing surface 118 is aligned with the dispenser port 44. Operation of the pressure system is discussed below.

The dose counting system 16 is mounted to the hopper 42 and includes a ribbon 128, having successive numbers or other suitable indicia printed thereon, in alignment with a transparent window 130 provided in the housing 18 (see FIG. 2). The dose counting system 16 includes a rotatable bobbin 132, an indexing spool 134 rotatable in a single direction, and the ribbon 128 rolled and received on the bobbin 132 and having a first end 127 secured to the spool 134, wherein the ribbon 128 unrolls from the bobbin 132 so that the indicia is successively displayed as the spool 134 is rotated or advanced.

The spool 134 is arranged to rotate upon movement of the yokes 66,68 to effect delivery of a dose of formulation from the reservoir 14 into the delivery passageway 34, such that the number on the ribbon 128 is advanced to indicate that another dose has been dispensed by the inhaler 10. The ribbon 128 can be arranged such that the numbers, or other suitable indicia, increase or decrease upon rotation of the spool 134. For example, the ribbon 128 can be arranged such that the numbers, or other suitable indicia, decrease upon rotation of the spool 134 to indicate the number of doses remaining in the inhaler 10.

Alternatively, the ribbon 128 can be arranged such that the numbers, or other suitable indicia, increase upon rotation of the spool 134 to indicate the number of doses dispensed by the inhaler 10.

The indexing spool 134 preferably includes radially extending teeth 136, which are engaged by a pawl 138 extending from one of the cam followers 78 (see FIGS. 3 and 11) of the second yoke 68 upon movement of the yoke to rotate, or advance, the indexing spool 134. More particularly, the pawl 138 is shaped and arranged such that it engages the teeth 136 and advances the indexing spool 134 only upon the mouthpiece 24 cover 28 being closed and the yokes 66,68 moved back towards the cap 26 of the housing 18.

Figure 14:
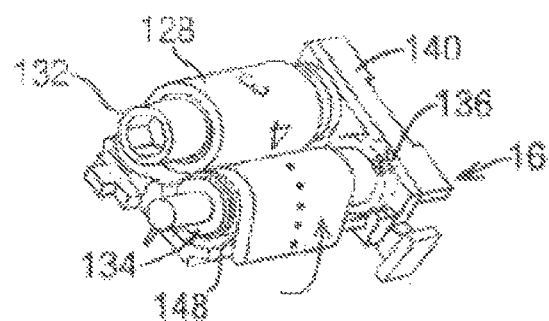
FIG. 14 is an enlarged isometric view of a dose counter of the inhaler of FIG. 1.
Figure 15:
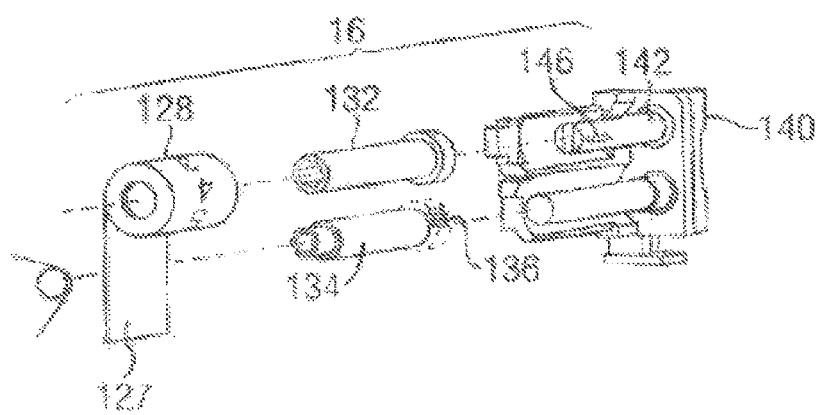
FIG. 15 is an exploded enlarged isometric view of the dose counter of the inhaler of FIG. 1.
Figure 16:
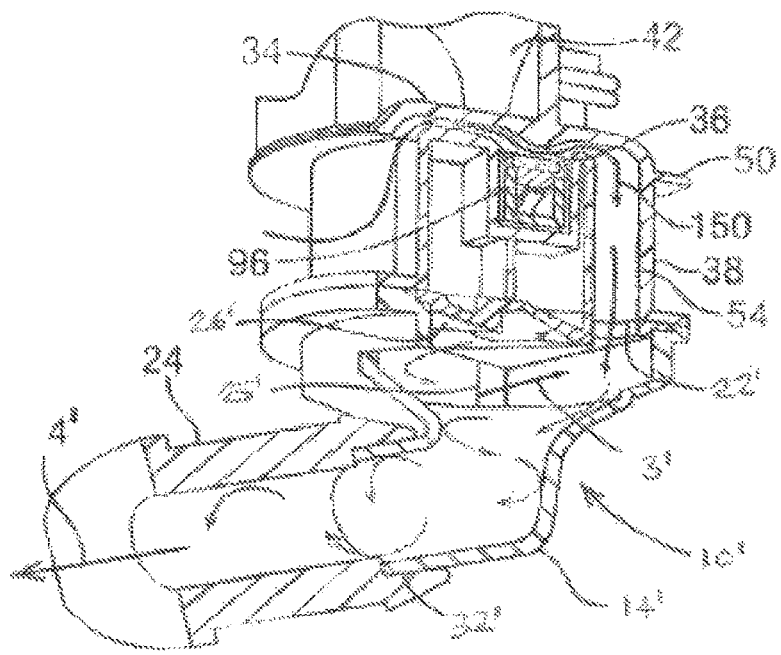
FIG. 16 is an enlarged isometric view, partially in section, of a portion of the inhaler of FIG. 1 illustrating formulation inhalation through the inhaler.
Figure 19:
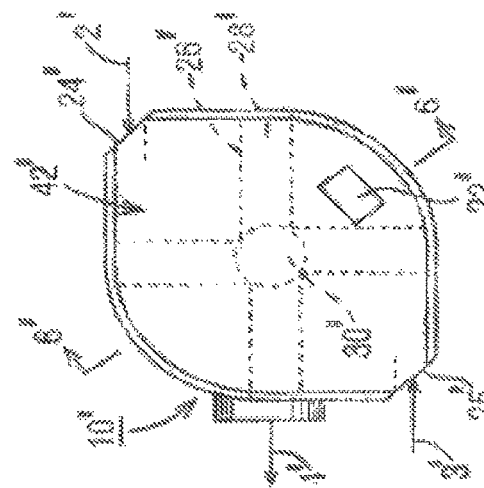
FIG. 19 is a top plan view of the deagglomerator of FIG. 17.
Figure 20:
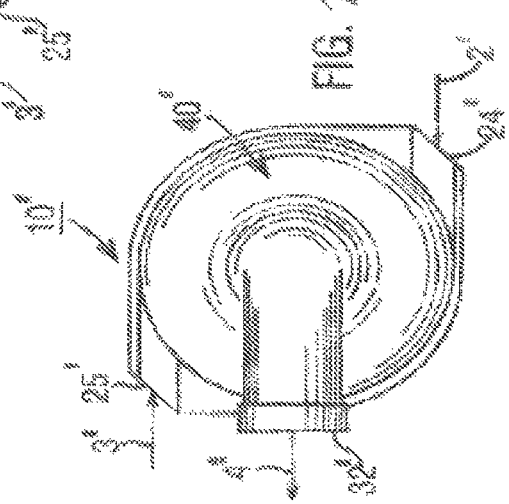
FIG. 20 is a bottom plan view of the deagglomerator of FIG. 17.
Figure 18:
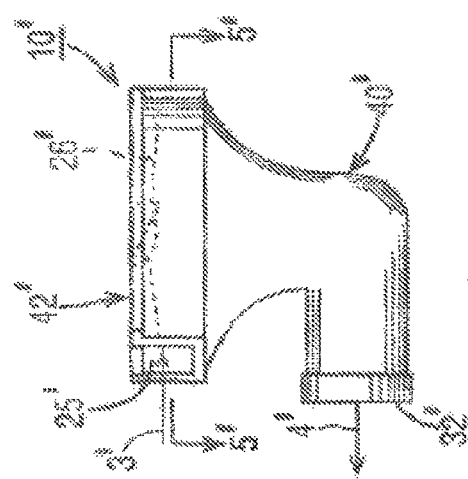
FIG. 18 is a side elevation view of the deagglomerator of FIG. 17.
Figure 21:
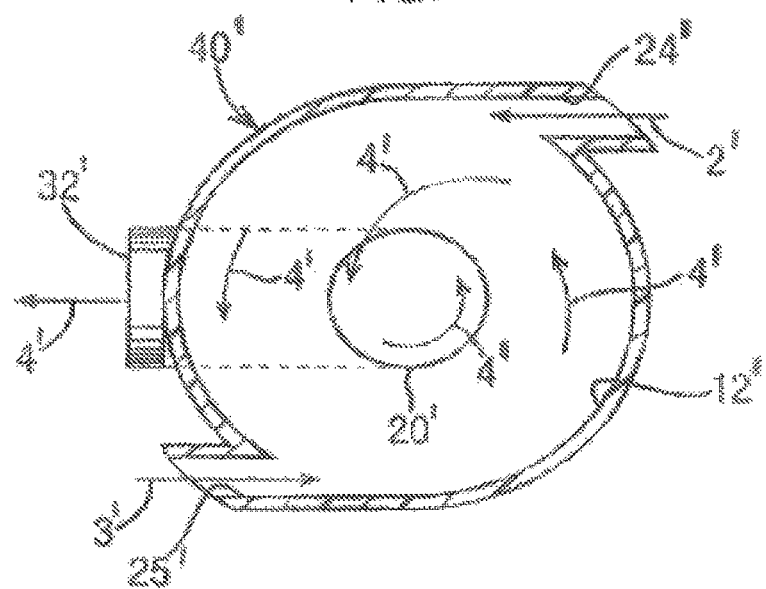
FIG. 21 is a sectional view of the deagglomerator of FIG. 17 taken along line 5'-5' of FIG. 18.
Figure 22:
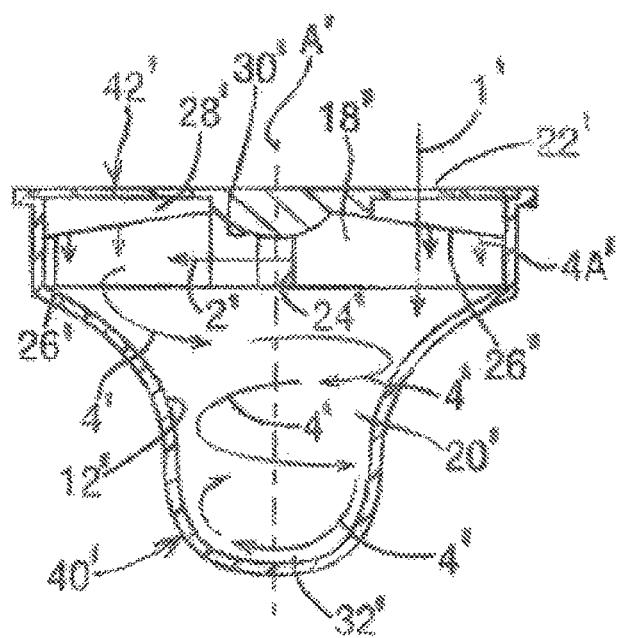
FIG. 22 is a sectional view of the deagglomerator of FIG. 17 taken along line 6'-6' of FIG. 19.

The dose counting system 16 also includes a chassis 140 that secures the dose counting system to the hopper 42 and includes shafts 142,144 for receiving the bobbin 132 and the indexing spool 134. The bobbin shaft 142 is preferably forked and includes radially nubs 146 for creating a resilient resistance to rotation of the bobbin 132 on the shaft 142. A clutch spring 148 is received on the end of the indexing spool 134 and locked to the chassis 140 to allow rotation of the spool 134 in only a single direction (anticlockwise as shown in FIG. 14). Operation of the dose counting system 16 is discussed below.

Figure 13:
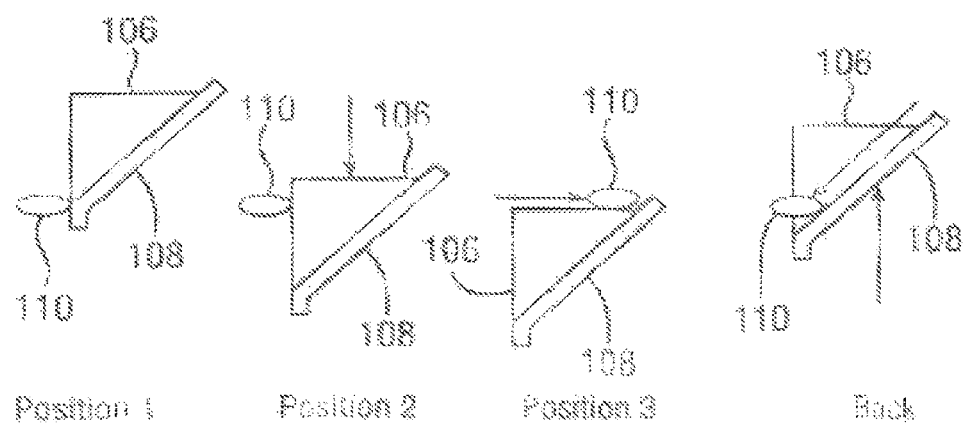
FIG. 13 is a schematic illustration of lateral movement of a boss of the formulation cup in response to longitudinal movement of the ratchet and the push bar of the yoke of the inhaler of FIG. 1.

FIG. 13 illustrates the relative movements of the boss 110 of the cup sled 100, and the ratchet 106 and the push bar 108 of the second yoke 68 as the mouthpiece cover 28 is opened and closed. In the first position of the yokes 66,68 (wherein the cover 28 is closed and the cam followers 78 are in contact with the first cam surfaces 90 of the cams 70), the ratchet 106 prevents the cup spring 104 from moving the cup sled 100 to the delivery passageway 34. The dose metering system is arranged such that when the yokes are in the first position, the recess 102 of the formulation cup 98 is directly aligned with the dispenser port 44 of the reservoir 14 and the pressure relief port 116 of the spacer 38 is sealed by the second sealing surface 124 of the cup sled 100.

Upon the cover 28 being partially opened such that the second cam surfaces 92 of the cams 70 engage the cam followers 78, the actuator spring 69 is allowed to move the yokes 66,68 linearly towards the mouthpiece 24 to the second position and partially collapse the bellows 40 of the formulation reservoir 14. The partially collapsed bellows 40 pressurizes the interior of the reservoir 14 and ensures formulation dispensed from the dispenser port 44 of the reservoir fills the recess 102 of the formulation cup 98 such that a predetermined dose is provided. In the second position, however, the ratchet 106 prevents the cup sled 100 from being moved to the delivery passageway 34, such that the recess 102 of the formulation cup 98 remains aligned with the dispenser port 44 of the reservoir 14 and the pressure relief port 116 of the spacer 38 remains sealed by the second sealing surface 124 of the cup assembly 96.

Upon the cover 28 being fully opened such that the third cam surfaces 94 engage the cam followers 78, the actuator spring 69 is allowed to move the yokes 66,68 further towards the mouthpiece 24 to the third position. When moved to the third position, the ratchet 106 disengages, or falls below the boss 110 of the cup sled 100 and allows the cup sled 100 to be moved by the cup spring 104, such that the filled recess 102 of the cup 98 is position in the venturi 36 of the delivery passageway 34 and the dispenser port 44 of the reservoir 14 is sealed by the first sealing surface 118 of the cup assembly 96. In addition, the pressure relief port 116 is uncovered by the indentation 126 in the side surface of the sled 100 to release pressure from the reservoir 14 and allow the bellows 40 to further collapse and accommodate the movement of the yokes 66,68 to the third position. The inhaler 10 is then ready for inhalation by a patient of the dose of formulation placed in the delivery passageway 34.

As shown in FIG. 16, a breath-induced air stream 4' diverted through the delivery passageway 34 passes through the venturi 36, entrains the formulation and carries the formulation into the deagglomerator 10' of the inhaler 10. Two other breath-induced air streams 2', 3' (only one shown) enter the deagglomerator 10' through the diametrically opposed inlet ports 24', 25' and combine with the formulation entrained air stream 150 from the delivery passageway 34. The combined flows 4' and entrained dry powder formulation then travel to the outlet port 32' of the deagglomerator and pass through the mouthpiece 24 for patient inhalation.

Once inhalation is completed, the mouthpiece cover 28 can be closed. When the cover 28 is closed, the trigger cams 70 force the yokes 66,68 upwardly such that the first yoke 66 expands the bellows 40, and the pawl 138 of the second yoke 68 advances the indexing spool 134 of the dose counting system 16 to provide a visual indication of a dose having been dispensed. In addition, the cup assembly 96 is forced back to the first position by the pusher bar 108 of the upwardly moving second yoke 68 (see FIG. 13) such that the boss 110 of the cup sled 100 is engaged and retained by the ratchet 106 of the second yoke 68.

The present invention will now be described with reference to the following examples which are not intended to be limiting.

EXAMPLES

Example 1

Preparation of Blend 7 (High Strength—Fp/Alb/α-Lactose Monohydrate)

Fluticasone propionate (Fp) was blended together with α-lactose monohydrate using a high speed mixing process operating at 750 rpm (revolutions per minute) at the 0.4 kg scale using a TangoMix blender. Albuterol sulfate (Alb) was blended together with α-lactose monohydrate carrier using a high speed mixing process operating at 750 rpm at the 0.4 kg scale using a TangoMix blender. An equal portion of the Fp-containing blend and the Alb-containing blend were then added together and hand-tumbled (360 degree rotations/50 times) to provide a final combination blend containing 0.52% fluticasone propionate (suitable for providing a 51 μg dose, size 4 dose cup) and 1.13% albuterol sulfate (suitable for providing a 90 μg dose, size 4 dose cup) at the 0.4 kg scale. The final combination blend was then filled into the reservoir of a dry powder inhaler device. The devices were placed on an unwrapped tray at 30° C./65% RH for 4 weeks for conditioning and then subjected to stability assessment. For comparison to ArmonAir data, 1 month in-use data has been used as time 0 as the ArmonAir product is equilibrated (conditioned) for 6 weeks at 30° C./65% RH. Data relating to this example can be found in FIGS. 24 and 25, and Tables 1 and 2 (as blend 7).

Example 2

Preparation of Blend 10 (Low Strength—Fp/Alb/α-Lactose Monohydrate)

Fluticasone propionate (Fp) was blended together with α-lactose monohydrate using a high speed mixing process operating at 750 rpm at the 0.5 kg scale using a TangoMix Blender. Albuterol sulfate (Alb) was blended together with α-lactose monohydrate carrier using a high shear mixing process operating at 750 rpm at the 0.5 kg scale using a TangoMix blender. An equal portion of the Fp-containing blend and the Alb-containing blend were then added together and hand-tumbled (360 degree rotations/50 Times) to provide a final combination blend containing 0.25% fluticasone propionate (suitable for providing a 25 μg dose, size 4 dose cup) and 1.13% albuterol sulfate (suitable for providing a 90 μg dose, size 4 dose cup) at the 0.5 kg scale. The final combination blend was then filled into the reservoir of a dry powder inhaler device. The devices were placed on an unwrapped tray at 30° C./65% RH for 4 weeks for conditioning and then subjected to stability assessment. For comparison to ArmonAir data, 1 month in-use data has been used as time 0 as the ArmonAir product is equilibrated (conditioned) for 6 weeks at 30° C./65% RH. Data relating to this example can be found in FIGS. 26 and 27, and Table 2 (see blend 10).

Example 3

Preparation of Blend 11 (Low Strength—Fp/Alb/α-Lactose Monohydrate/Magnesium Stearate)

The α-lactose monohydrate carrier was hand-tumbled (360 degree rotations/50 times) with 0.5% magnesium stearate (MS) at the 0.5 kg scale. Fluticasone Propionate (Fp) was blended with the 0.5% MS/α-lactose monohydrate carrier using a high speed mixing process operating at 750 rpm at the 0.5 kg scale. Albuterol sulfate (Alb) was blended together with the 0.5% MS/α-lactose monohydrate using a high speed mixing process operating at 750 rpm at the 0.5 kg scale. An equal portion of the Fp-containing blend and the Alb-containing blend were then added together and hand-tumbled (360 degree rotations/50 Times) to provide a final combination blend containing 0.25% fluticasone propionate (suitable for providing a 25 μg dose, size 4 dose cup) and 1.13% albuterol sulfate (suitable for providing a 90 μg dose, size 4 dose cup) and 0.5% MS at the 0.5 kg scale. The final combination blend was then filled into the reservoir of a dry powder inhaler device. The devices were placed on an unwrapped tray at 30° C./65% RH for 4 weeks for conditioning and then subjected to stability assessment. For comparison to ArmonAir data, 1 month in-use data has been used as time 0 as the ArmonAir product is equilibrated (conditioned) for 6 weeks at 30° C./65% RH. Data relating to this example can be found in FIGS. 26 and 27 and Table 1 (see blend 11).

Comparative Example 1

Preparation of RD1404 (High Strength—Fp/α-Lactose Monohydrate)

Fluticasone propionate (Fp) was blended together with an α-lactose monohydrate carrier using a high speed mixing process in a blender operating at 120 rpm to provide a mono-product containing 0.49% fluticasone propionate (suitable for providing a 51 mcg dose, size 4 dose cup). The final mono-product blend was then filled into the reservoir of a dry powder inhaler device. The devices were then placed on a tray that was wrapped by a polyethylene bag and conditioned for 6 weeks at 30° C./65% RH. Following the conditioning step, the devices were then placed on a CRT (wrapped with desiccant at 25° C./60% RH) for 6 months followed by in-use assessment (30° C./65% RH, unwrapped) at 1 month and 2 months. Data relating to this example can be found in FIGS. 24 and 25, and Tables 1 and 2 (see RD1404, ArmonAir Registration Batch).

Comparative Example 2

Preparation of RD1119 (Low Strength—Fp/α-Lactose Monohydrate)

Fluticasone propionate (Fp) was blended together with an α-lactose monohydrate carrier using a high speed mixing process in a blender operating at 120 rpm to provide a mono-product containing 0.49% fluticasone propionate (suitable for providing a 25 mcg dose, size 3 dose cup). The final mono-product blend was then filled into the reservoir of a dry powder inhaler device. The devices were then placed on a tray that was wrapped by a polyethylene bag and conditioned for 6 weeks at 30° C./65% RH. Following the conditioning step, the devices were then placed on a CRT (wrapped with desiccant at 25° C./60% RH) for 6 months followed by in-use assessment (30° C./65% RH, unwrapped) at 1 month and 2 month. Data relating to this example can be found in FIGS. 26 and 27, and Table 1 (see RD1119).

All percentages given in the examples and comparative example are percentages by weight of the total composition.

The key in the figures read top-to-bottom corresponds to the bars read left-to-right.

Table 1 shows the relative change in stability of the blends contained within Examples 1 to 3 and the Comparative Examples 1 to 2, respectively. These data show the amount of fluticasone propionate present within the respective combination blends at $T_1$ (1 month) and after 6 months under in-use conditions (unwrapped at 30° C./65% relative humidity) when compared to the ArmonAir Respiclick mono products at T0 (equilibrated for 6 weeks) and after 6 months under the same conditions.

Table 2 shows the relative change in the amount of fluticasone propionate for Comparative Example 1 (containing fluticasone propionate as the sole active ingredient) over two months and Example 1/blend 7 (containing both fluticasone propionate and albuterol sulfate as active ingredients) over five months.

The amount of active ingredient was calculated using ultra-performance liquid chromatography (UPLC).

UPLC chromatography was performed using a Waters Acquity UPLC system equipped with a Waters Acquity UPLC CSH Phenyl-Hexyl, 1.7 μm, 50 mm×2.1 mm column with an inline filter. The sample was dissolved in a MeOH:MeCN:water (40:40:20) diluent, and purified using gradient elution of two mobile phases A and B. Mobile phase A being 100% buffer solution (20 mM sodium dihydrogen phosphate having a pH pf 3.1 adjusted with 85% orthophosphoric acid) and mobile phase B being 100% acetonitrile. The UV wavelength on the detector set was set to 238 nm.

TABLE 1

The relative change in the amount of fluticasone propionate for the blends mentioned in Examples 1 to 3 and Comparative examples 1 to 2 (RD1404 and RD1119 contain fluticasone propionate as the sole active ingredient. Blends 7 (Example 1), 10 (Example 2) and 11 (Example 3) each contain both fluticasone propionate and albuterol sulfate as active ingredients)

| Impactor stage grouping | RD1404 at T0 (μg) | RD1404 unwrapped at 2 months (μg) | 2 months loss/gain (μg) | Stage 2 to MOC loss/gain (μg) |
|---|---|---|---|---|
| 1 (AD-stage 1) | 34.57 | 35.18 | 0.61 | −3.65 |
| 2 (stage 2-5) | 17.92 | 14.59 | −3.33 | |
| 3 (stage 6-micro orifice collector, MOC) | 0.56 | 0.24 | −0.32 | |

| Impactor stage grouping | Blend 7 unwrapped at 1 month (μg) | Blend 7 unwrapped at 6 months (μg) | 5 months (loss/gain (μg)) | Stage 2 to MOC (μg) |
|---|---|---|---|---|
| 1 (AD-stage 1) | 38.02 | 40.99 | 2.97 | 0.48 |
| 2 (stage 2-5) | 13.91 | 14.32 | 0.41 | |
| 3 (stage 6-micro orifice collector, MOC) | 0.68 | 0.75 | 0.07 | |

| Impactor stage grouping | RD1119 at T0 (μg) | RD1119 unwrapped at 1 month (μg) | 1 month loss/gain (μg) | Stage 2 to MOC loss/gain (μg) |
|---|---|---|---|---|
| 1 (AD-stage 1) | 16.2 | 16.6 | 0.4 | −0.4 |
| 2 (stage 2-5) | 8.6 | 8.2 | −0.4 | |
| 3 (stage 6-micro orifice collector, MOC) | 0.1 | 0.1 | 0 | |

| Impactor stage grouping | Blend 10 unwrapped at 1 month (μg) | Blend 10 unwrapped at 6 months (μg) | 5 months (loss/gain (μg)) | Stage 2 to MOC (μg) |
|---|---|---|---|---|
| 1 (AD-stage 1) | 21.39 | 22.17 | 0.83 | 0.14 |
| 2 (stage 2-5) | 6.30 | 6.31 | 0.01 | |
| 3 (stage 6-micro orifice collector, MOC) | 0.42 | 0.55 | 0.13 | |

| Impactor stage grouping | Blend 11 unwrapped at 1 month (μg) | Blend 11 unwrapped at 6 months (μg) | 5 months (loss/gain (μg)) | Stage 2 to MOC (μg) |
|---|---|---|---|---|
| 1 (AD-stage 1) | 16.98 | 17.77 | 0.79 | 0.08 |
| 2 (stage 2-5) | 8.85 | 8.78 | −0.07 | |
| 3 (stage 6-micro orifice collector, MOC) | 2.95 | 3.10 | 0.15 | |

TABLE 2

The relative change in the amount of fluticasone propionate for Comparative Example 1 (containing fluticasone propionate as the sole active ingredient) and Blend 7 (containing both fluticasone propionate and albuterol sulfate as active ingredients)

| Parameter | RD1404 at T0 (μg) | RD1404 unwrapped at 1 months (μg) | RD1404 unwrapped at 2 months (μg) | % Difference over two months |
|---|---|---|---|---|
| FPF | 31.42 | 27.37 | 26.02 | −17.19 |
| MMAD | 2.76 | 3.07 | 3.13 | +13.41 |
| FPM | 16.67 | 13.80 | 13.02 | −21.90 |
| Group 1 (AD-stage 1) | 34.57 | 34.81 | 35.18 | +1.77 |
| Group 2 (stage 2-5) | 17.92 | 15.35 | 14.59 | −18.58 |
| Group 3 (stage 6-micro orifice collector, MOC) | 0.56 | 0.27 | 0.24 | −57.14 |

| Parameter | Blend 7 unwrapped at 1 month (μg) | Blend 7 unwrapped at 3 months (μg) | Blend 7 unwrapped at 6 months (μg) | % Difference over five months |
|---|---|---|---|---|
| FPF | 25.01 | 23.72 | 24.12 | −3.56 |
| MMAD | 2.77 | 2.85 | 2.87 | +3.61 |
| FPM | 13.16 | 12.68 | 13.52 | +2.74 |
| Group 1 (AD-stage 1) | 38.02 | 39.35 | 40.99 | +7.81 |
| Group 2 (stage 2-5) | 13.90 | 13.44 | 14.32 | +3.02 |
| Group 3 (stage 6-micro orifice collector, MOC) | 25.01 | 23.72 | 24.12 | −3.56 |

The invention claimed is:

1. A method for the treatment of acute exacerbations of asthma or COPD in a subject in need thereof, comprising administering to the subject pro re nata rescue medication of a dry powder inhalable formulation consisting of fluticasone propionate, albuterol sulfate and α-lactose monohydrate, wherein a total administered daily dose of fluticasone propionate does not exceed 1,000 μg.

2. The method of claim 1, wherein the method treats asthma in patients with step 2 asthma as defined by the Global Initiative for Asthma (GINA) 2005 guidelines.

3. The method of claim 1, wherein the method treats COPD in patients with airflow limitation severity GOLD 2 as defined by the committee for the Global Initiative for Chronic Obstructive Lung Disease (GOLD) 2017 guidelines.

* * * * *